(12) United States Patent
Wham et al.

(10) Patent No.: US 9,901,385 B2
(45) Date of Patent: *Feb. 27, 2018

(54) SYSTEMS AND METHODS FOR MULTIFREQUENCY CABLE COMPENSATION

(71) Applicant: COVIDIEN LP, Mansfield, MA (US)

(72) Inventors: Robert H. Wham, Boulder, CO (US); Andrey Y. Belous, Longmont, CO (US); Alexander M. Waskiewicz, Lafayette, CO (US); Anthony D. Ricke, Boulder, CO (US)

(73) Assignee: COVIDIEN LP, Mansfield, MA (US)

( * ) Notice: Subject to any disclaimer, the term of this patent is extended or adjusted under 35 U.S.C. 154(b) by 631 days.

This patent is subject to a terminal disclaimer.

(21) Appl. No.: 14/534,372

(22) Filed: Nov. 6, 2014

(65) Prior Publication Data
US 2015/0196344 A1    Jul. 16, 2015

Related U.S. Application Data

(60) Provisional application No. 61/926,570, filed on Jan. 13, 2014, provisional application No. 61/926,586, filed on Jan. 13, 2014.

(51) Int. Cl.
*A61B 18/12* (2006.01)
*A61B 18/14* (2006.01)
(Continued)

(52) U.S. Cl.
CPC .......... *A61B 18/1206* (2013.01); *A61B 18/00* (2013.01); *A61B 18/1445* (2013.01);
(Continued)

(58) Field of Classification Search
CPC ............ A61B 18/1206; A61B 18/1233; A61B 18/1445
See application file for complete search history.

(56) References Cited

U.S. PATENT DOCUMENTS

| 4,961,047 A | 10/1990 | Carder |
| 5,175,472 A * | 12/1992 | Johnson, Jr. ............. H05H 7/02 313/231.31 |

(Continued)

FOREIGN PATENT DOCUMENTS

| DE | 179607 C | 3/1905 |
| DE | 390937 C | 3/1924 |

(Continued)

OTHER PUBLICATIONS

Examination Report issued in corresponding EP Application No. 14 200 063.7, dated Jan. 20, 2017, 6 pages.
(Continued)

*Primary Examiner* — William Levicky

(57) ABSTRACT

The electrosurgical systems and methods of the present disclosure perform cable compensation using an electrosurgical generator that includes a plurality of sensors configured to sense voltage and current waveforms, a plurality of medium-band filters, a plurality of narrowband filters, and a signal processor. The plurality of medium-band filters and narrowband filters pass sensed voltage and current waveforms at a plurality of predetermined frequencies. The signal processor calculates medium-band RMS voltage and current values using the output from the plurality of medium-band filters, calculates narrowband phase and magnitude values using the output from the plurality of narrowband filters, calculates tissue impedance based on the medium-band RMS voltage and current values and the narrowband phase value, and generates a control signal to control the energy generated by the electrosurgical generator based on the calculated tissue impedance.

20 Claims, 11 Drawing Sheets

(51) Int. Cl.
*A61B 18/00* (2006.01)
*A61B 17/00* (2006.01)

(52) U.S. Cl.
CPC .......... *A61B 2017/0003* (2013.01); *A61B 2018/0063* (2013.01); *A61B 2018/00577* (2013.01); *A61B 2018/00589* (2013.01); *A61B 2018/00601* (2013.01); *A61B 2018/00648* (2013.01); *A61B 2018/00672* (2013.01); *A61B 2018/00702* (2013.01); *A61B 2018/00779* (2013.01); *A61B 2018/00827* (2013.01); *A61B 2018/00851* (2013.01); *A61B 2018/00857* (2013.01); *A61B 2018/00869* (2013.01); *A61B 2018/00875* (2013.01); *A61B 2018/00892* (2013.01); *A61B 2018/128* (2013.01)

(56) References Cited

U.S. PATENT DOCUMENTS

| | | | |
|---|---|---|---|
| 6,942,660 | B2 | 9/2005 | Pantera et al. |
| 6,966,907 | B2 | 11/2005 | Goble |
| 7,300,435 | B2 | 11/2007 | Wham et al. |
| D574,323 | S | 8/2008 | Waaler |
| 7,651,492 | B2 * | 1/2010 | Wham .......... A61B 18/1206 606/34 |
| 7,799,020 | B2 | 9/2010 | Shores et al. |
| 8,242,782 | B2 | 8/2012 | Brannan et al. |
| 8,248,075 | B2 | 8/2012 | Brannan et al. |
| 8,287,527 | B2 | 10/2012 | Brannan et al. |
| 2005/0046496 | A1 | 3/2005 | Singh |
| 2006/0224152 | A1 | 10/2006 | Behnke et al. |
| 2009/0082765 | A1 | 3/2009 | Collins et al. |
| 2011/0071521 | A1 | 3/2011 | Gilbert |
| 2011/0087213 | A1 | 4/2011 | Messerly et al. |
| 2011/0098695 | A1 | 4/2011 | Brannan |
| 2012/0265194 | A1 | 10/2012 | Podhajsky |
| 2012/0265195 | A1 | 10/2012 | Gilbert |
| 2013/0197510 | A1 | 8/2013 | Heckel |
| 2013/0197874 | A1 | 8/2013 | Heckel |

FOREIGN PATENT DOCUMENTS

| | | |
|---|---|---|
| DE | 1099658 B | 2/1961 |
| DE | 1139927 B | 11/1962 |
| DE | 1149832 B | 6/1963 |
| DE | 1439302 A1 | 1/1969 |
| DE | 2439587 A1 | 2/1975 |
| DE | 2455174 A1 | 5/1975 |
| DE | 2407559 A1 | 8/1975 |
| DE | 2602517 A1 | 7/1976 |
| DE | 2504280 A1 | 8/1976 |
| DE | 2540968 A1 | 3/1977 |
| DE | 2820908 A1 | 11/1978 |
| DE | 2803275 A1 | 8/1979 |
| DE | 2823291 A1 | 11/1979 |
| DE | 2946728 A1 | 5/1981 |
| DE | 3143421 A1 | 5/1982 |
| DE | 3045996 A1 | 7/1982 |
| DE | 3120102 A1 | 12/1982 |
| DE | 3510586 A1 | 10/1986 |
| DE | 3604823 A1 | 8/1987 |
| DE | 3904558 A1 | 8/1990 |
| DE | 3942998 A1 | 7/1991 |
| DE | 4206433 A1 | 9/1993 |
| DE | 4339049 A1 | 5/1995 |
| DE | 19506363 A1 | 8/1996 |
| DE | 19717411 A1 | 11/1998 |
| DE | 19848540 A1 | 5/2000 |
| DE | 20014128 U1 | 3/2001 |
| DE | 10 2008058737 A1 | 4/2010 |
| EP | 0 246 350 A1 | 11/1987 |
| EP | 267403 A2 | 5/1988 |
| EP | 296777 A2 | 12/1988 |
| EP | 310431 A2 | 4/1989 |
| EP | 325456 A2 | 7/1989 |
| EP | 336742 A2 | 10/1989 |
| EP | 390937 A1 | 10/1990 |
| EP | 0 556 705 A1 | 8/1993 |
| EP | 608609 A2 | 8/1994 |
| EP | 0 836 868 A2 | 4/1998 |
| EP | 880220 A2 | 11/1998 |
| EP | 0 882 955 A1 | 12/1998 |
| EP | 1051948 A2 | 11/2000 |
| EP | 1366724 A1 | 12/2003 |
| EP | 1776929 A1 | 4/2007 |
| FR | 1 275 415 A | 11/1961 |
| FR | 1 347 865 A | 1/1964 |
| FR | 2 313 708 A1 | 12/1976 |
| FR | 2364461 A1 | 4/1978 |
| FR | 2 502 935 A1 | 10/1982 |
| FR | 2 517 953 A1 | 6/1983 |
| FR | 2 573 301 A1 | 5/1986 |
| JP | 63 005876 A | 1/1988 |
| JP | 2002-065690 A | 3/2002 |
| JP | 2005-185657 A | 7/2005 |
| SU | 166452 | 11/1964 |
| SU | 727201 A2 | 4/1980 |
| WO | 02/11634 A1 | 2/2002 |
| WO | 02/45589 A2 | 6/2002 |
| WO | 03/090635 A1 | 11/2003 |
| WO | 06/050888 A1 | 5/2006 |
| WO | 08/053532 A1 | 5/2008 |
| WO | 2011126580 A2 | 10/2011 |
| WO | 2013019702 A1 | 2/2013 |

OTHER PUBLICATIONS

European Search Report issued in corresponding EP Application No. 14200063.7 dated Jun. 30, 2015.
U.S. Appl. No. 14/297,812 dated Jun. 6, 2014, inventor: Wham.
U.S. Appl. No. 14/297,890 dated Jun. 6, 2014, inventor: Wham.
U.S. Appl. No. 14/320,762 dated Jul. 1, 2014, inventor: Gilbert.
U.S. Appl. No. 14/320,804 dated Jul. 1, 2014, inventor: Gilbert.
Wald et al., "Accidental Burns", JAMA, Aug. 16, 1971, vol. 217, No. 7, pp. 916-921.
Vallfors et al., "Automatically Controlled Bipolar Electrosoagulation-'COA-COMP'", Neurosurgical Review 7:2-3 (1984) pp. 187-190.
Sugita et al., "Bipolar Coagulator with Automatic Thermocontrol", J. Neurosurg., vol. 41, Dec. 1944, pp. 777-779.
Prutchi et al. "Design and Development of Medical Electronic Instrumentation", John Wiley & Sons, Inc. 2005.
Momozaki et al. "Electrical Breakdown Experiments with Application to Alkali Metal Thermal-to-Electric Converters", Energy conversion and Management; Elsevier Science Publishers, Oxford, GB; vol. 44, No. 6, Apr. 1, 2003 pp. 819-843.
Muller et al. "Extended Left Hemicolectomy Using the LigaSure Vessel Sealing System", Innovations That Work; Company Newsletter; Sep. 1999.
"Electrosurgical Unit Analyzer ESU-2400 Series User Manual" Apr. 1, 2002; Retrieved from Internet: <URL:http://www.bcgroupintl.com/ESU_2400/Updates/ESU-2400_UM_Rev04.pdf>, pp. 6, 11, 73.
Ogden Goertzel Alternative to the Fourier Transform: Jun. 1993 pp. 485-487, Electronics World; Reed Business Publishing, Sutton, Surrey, BG vol. 99, No. 9. 1687.
Hadley I C D et al., "Inexpensive Digital Thermometer for Measurements on Semiconductors", International Journal of Electronics; Taylor and Francis. Ltd.; London, GB; vol. 70, No. 6 Jun. 1, 1991; pp. 1155-1162.
Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Richard Wolf Medical Instruments Corp. Brochure, "Kleppinger Bipolar Forceps & Bipolar Generator", 3 pp. Jan. 1989.
Astrahan, "A Localized Current Field Hyperthermia System for Use with 192-Iridium Interstitial Implants" Medical Physics, 9 (3), May/Jun. 1982.

(56) References Cited

OTHER PUBLICATIONS

Alexander et al., "Magnetic Resonance Image-Directed Stereotactic Neurosurgery: Use of Image Fusion with Computerized Tomography to Enhance Spatial Accuracy", Journal Neurosurgery, 83; (1995) pp. 271-276.
Geddes et al., "The Measurement of Physiologic Events by Electrical Impedance", Am. J. MI, Jan. Mar. 1964, pp. 16-27.
Cosman et al., "Methods of Making Nervous System Lesions", In William RH, Rengachary SS (eds): Neurosurgery, New York: McGraw-Hill, vol. 111, (1984), pp. 2490-2499.
Anderson et al., "A Numerical Study of Rapid Heating for High Temperature Radio Frequency Hyperthermia" International Journal of Bio-Medical Computing, 35 (1994) pp. 297-307.
Benaron et al., "Optical Time-of-Flight and Absorbance Imaging of Biologic Media", Science, American Association for the Advancement of Science, Washington, DC, vol. 259, Mar. 5, 1993, pp. 1463-1466.
Cosman et al., "Radiofrequency Lesion Generation and Its Effect on Tissue Impedance", Applied Neurophysiology 51: (1988) pp. 230-242.
Zlatanovic M., "Sensors in Diffusion Plasma Processing" Microelectronics 1995; Proceedings 1995; 20th International Conference CE on Nis, Serbia Sep. 12-14, 1995; New York, NY vol. 2 pp. 565-570.
Ni W. et al. "A Signal Processing Method for the Coriolis Mass Flowmeter Based on a Normalized . . . ", Journal of Applied Sciences—Yingyong Kexue Xuebao, Shangha CN, vol. 23 No. 2;(Mar. 2005); pp. 160-164.
Chicharo et al. "A Sliding Goertzel Algorith" Aug. 1996, pp. 283-297, Signal Processing, Elsevier Science Publishers B.V. Amsterdam, NL vol. 52 No. 3.
Bergdahl et al., "Studies on Coagulation and the Development of an Automatic Computerized Bipolar Coagulator" Journal of Neurosurgery 75:1, (Jul. 1991) pp. 148-151.
Cosman et al., "Theoretical Aspects of Radiofrequency Lesions in the Dorsal Root Entry Zone", Neurosurgery 15: (1984) pp. 945-950.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
Medtrex Brochure—Total Control at Full Speed, "The O.R. Pro 300", 1 p. Sep. 1998.
Valleylab Brochure "Valleylab Electroshield Monitoring System", 2 pp. Nov. 1995.
U.S. Appl. No. 10/406,690 dated Apr. 3, 2003 inventor: Behnke.
U.S. Appl. No. 10/573,713 dated Mar. 28, 2006 inventor: Wham.
U.S. Appl. No. 10/761,524 dated Jan. 21, 2004 inventor: Wham.
U.S. Appl. No. 11/242,458 dated Oct. 3, 2005 inventor: Becker.
U.S. Appl. No. 14/096,341 dated Dec. 4, 2013 inventor: Johnson.
U.S. Appl. No. 14/098,859 dated Dec. 6, 2013 inventor: Johnson.
U.S. Appl. No. 14/100,113 dated Dec. 9, 2013 inventor: Gilbert.
U.S. Appl. No. 14/147,294 dated Jan. 3, 2014 inventor: Gilbert.
U.S. Appl. No. 14/147,312 dated Jan. 3, 2014 inventor: Gilbert.
U.S. Appl. No. 14/168,296 dated Jan. 30, 2014, inventor: Mattmiller.
U.S. Appl. No. 14/174,551 dated Feb. 6, 2014 inventor: Johnson.
U.S. Appl. No. 14/174,607 dated Feb. 6, 2014 inventor: Friedrichs.
U.S. Appl. No. 14/179,724 dated Feb. 13, 2014 inventor: Johnson.
U.S. Appl. No. 14/180,965 dated Feb. 14, 2014 inventor: Larson.
U.S. Appl. No. 14/181,114 dated Feb. 14, 2014 inventor: Larson.
U.S. Appl. No. 14/182,797 dated Feb. 18, 2014 inventor: Wham.
U.S. Appl. No. 14/190,830 dated Feb. 26, 2014 inventor: Johnson.
U.S. Appl. No. 14/190,895 dated Feb. 26, 2014 inventor: Gilbert.
U.S. Appl. No. 14/255,051 dated Apr. 17, 2014 inventor: Coulson.
U.S. Appl. No. 14/262,219 dated Apr. 25, 2014, inventor: Gilbert.
U.S. Appl. No. 14/267,066 dated May 1, 2014, inventor: Friedrichs.
U.S. Appl. No. 14/268,187 dated May 2, 2014, inventor: Kerr.
U.S. Appl. No. 14/283,604 dated May 21, 2014, inventor: Behnke.
U.S. Appl. No. 14/297,771 dated Jun. 6, 2014, inventor: Wham.

\* cited by examiner

SYSTEMS AND METHODS FOR MULTIFREQUENCY CABLE COMPENSATION

CROSS-REFERENCE TO RELATED APPLICATIONS

This application claims the benefit of, and priority to, U.S. Provisional Patent Application Nos. 61/926,570 and 61/926,586, both of which were filed on Jan. 13, 2013. This application is related to U.S. patent application Ser. No. 14/534,695 filed on Nov. 6, 2014. The entire contents of each of the above applications are hereby incorporated herein by reference.

BACKGROUND

1. Technical Field

The present disclosure relates to electrosurgery. More particularly, the present disclosure relates to electrosurgical systems and methods for compensating for the impedance of a cable used to deliver electrosurgical energy to tissue when the electrosurgical energy has energy at frequencies other than a fundamental frequency.

2. Background of Related Art

Electrosurgery involves the application of high-frequency electric current to cut or modify biological tissue during an electrosurgical operation. Electrosurgery is performed using an electrosurgical generator, an active electrode, and a return electrode. The electrosurgical generator (also referred to as a power supply or waveform generator) generates an alternating current (AC), which is applied to a patient's tissue through the active electrode and is returned to the electrosurgical generator through the return electrode. The alternating current typically has a frequency above 100 kilohertz (kHz) to avoid muscle and/or nerve stimulation.

During electrosurgery, the AC generated by the electrosurgical generator is conducted through tissue disposed between the active and return electrodes. The electrical energy (also referred to as electrosurgical energy) delivered to the tissue is converted into heat due to the resistivity of the tissue, which causes the tissue temperature to rise. The electrosurgical generator controls the heating of the tissue by controlling the electric power (i.e., electrical energy per time) provided to the tissue. Although many other variables affect the total heating of the tissue, increased current density and resistance of the tissue usually lead to increased heating. The electrosurgical energy is typically used for cutting, dissecting, ablating, coagulating, and/or sealing tissue.

The two basic types of electrosurgery employed are monopolar and bipolar electrosurgery. Both of these types of electrosurgery use an active electrode and a return electrode. In bipolar electrosurgery, the surgical instrument includes an active electrode and a return electrode on the same instrument or in very close proximity to one another, which cause current to flow through a small amount of tissue. In monopolar electrosurgery, the return electrode is located elsewhere on the patient's body and is typically not a part of the electrosurgical instrument itself. In monopolar electrosurgery, the return electrode is part of a device typically referred to as a return pad.

Electrosurgical generators make use of voltage and current sensors to measure quantities, such as power and tissue impedance, for controlling the output of the electrosurgical generator to achieve a desired clinical effect. The voltage and current sensors are often located inside the electrosurgical generators to save costs associated with incorporating sensors into the surgical instruments.

A cable, which may be more than a meter in length, connects the electrosurgical generator to the active and return electrodes and is used to deliver electrosurgical energy to tissue being treated. Every cable has an impedance that includes an inductance, a capacitance, and a resistance. This impedance can change the amount of actual energy delivered to the tissue in two ways. For a low load impedance, the inductance and resistance of the cable reduces the amount of voltage delivered to the tissue proportional to the amount of current, that is, as the current increases, the voltage drop across the cable will also increase. For a high load impedance, as the voltage increases, the amount of current flowing through the capacitance of the cable increases. This reduces the amount of current that is delivered to the tissue and adds distortions to the voltage and current waveforms so that they deviate from the desired pure sinusoidal, rectangular, sawtooth, pulse, triangular, or blended waveforms commonly used for electrosurgery.

Additionally, certain types of waveforms, such as pulse waveforms, have a significant amount of energy at frequencies other than the fundamental frequency. Thus, to more accurately measure power and impedance, many generators employ compensation algorithms that account for the cable impedance. These compensation algorithms typically involve solving Kirchhoff current and voltage equations for multiple nodes in a circuit model that models the impedance in the generator and cable as a circuit network. However, solutions to these equations, when implemented by a real-time embedded software system, may require a significant amount of memory and processing power.

SUMMARY

The electrosurgical systems and methods of the present disclosure accurately determine the energy that is actually delivered to tissue by compensating for the energy lost in an electrosurgical cable using complex current and phase signals at multiple frequencies measured at the output of an electrosurgical generator.

In one aspect, the present disclosure features an electrosurgical generator that generates energy to treat tissue and transmits the energy to the tissue via an electrosurgical cable. The electrosurgical generator includes a voltage sensor that senses a voltage waveform of the generated energy, a current sensor that senses a current waveform of the generated energy, a first medium-band filter that passes the sensed voltage waveform having at least one frequency within a first medium-band range of frequencies including a harmonic frequency, a second medium-band filter that passes the sensed current waveform having at least one frequency within the first medium-band range of frequencies including the harmonic frequency, a first narrowband filter that obtains narrowband phase and magnitude values of at least one frequency of the sensed voltage waveform within the first medium-band range of frequencies, a second narrowband filter that obtains narrowband phase and magnitude values of at least one frequency of the sensed current waveform within the first medium-band range of frequencies, and a signal processor. The signal processor determines medium-band root-mean-square (RMS) voltage and current values based on the sensed voltage and current waveforms filtered by the first and second medium-band filters, estimates the impedance of the tissue based on the narrowband magnitude and phase and the medium-band RMS voltage and current values; and generates a control signal to control the electrosurgical generator to generate energy based on the estimated impedance of the tissue.

The voltage and current waveforms may include sinusoidal waveforms, square waveforms, rectangular waveforms, triangular waveforms, spiked waveforms, trapezoidal waveforms, and/or sawtooth waveforms. The voltage and current waveforms may include harmonic distortion.

The electrosurgical generator may include a third medium-band filter that passes the sensed voltage waveform having a frequency within a second medium-band range of frequencies including a third harmonic frequency, a fourth medium-band filter that passes the sensed current waveform having at least one frequency within the second medium-band range of frequencies including the third harmonic frequency, a third narrowband filter that obtains narrowband phase and magnitude values of at least one frequency of the sensed voltage waveform within the second medium-band range of frequencies, and a fourth narrowband filter that obtains narrowband phase and magnitude values of at least one frequency of the sensed current waveform within the second medium-band range of frequencies. The harmonic frequency may be a fundamental frequency.

The electrosurgical generator may include a fifth medium-band filter that passes the sensed voltage waveform having a frequency within a third medium-band range of frequencies including a fifth harmonic frequency, a sixth medium-band filter that passes the sensed current waveform having a frequency within the third medium-band range of frequencies including the fifth harmonic frequency, a fifth narrowband filter that obtains narrowband phase and magnitude values of at least one frequency of the sensed voltage waveform within the third medium-band range of frequencies, and a sixth narrowband filter that obtains narrowband phase and magnitude values of at least one frequency of the sensed current waveform within the third medium-band range of frequencies.

The first medium-band range of frequencies may include sidebands to the harmonic frequency and/or ringing frequencies.

The first and second narrowband filters may be Goertzel filters and the first and second medium-band filters may be bandpass filters.

The signal processor may determine medium-band RMS voltage and current values based on the sensed voltage and current waveforms filtered by the third and fourth medium-band filters, calculate a total RMS voltage value by summing the RMS voltage values, and calculate a total RMS current value by summing the RMS current values. The signal processor may select frequencies from within the first and second medium-band ranges of frequencies and calculate weights for the medium-band RMS voltage and current values at the selected frequencies based on the narrowband magnitudes. The weights may be percentages of the narrowband magnitudes at the selected frequencies with respect to the sum of all narrowband magnitudes. A frequency may be selected if a narrowband magnitude at that frequency is greater than or equal to a predetermined value.

The weights may be percentages based on ratios between the medium-band RMS voltage values of a medium-band range of frequencies including a selected frequency and the total RMS voltage value, or ratios between the medium-band RMS current values of a medium-band range of frequencies including a selected frequency and the total RMS current value.

The signal processor may calculate weighted RMS voltage and current values at the selected frequencies and calculate the weighted powers based on the weighted RMS voltage and current values. The RMS voltage values and the RMS current values may be calculated by using a two-port network model of the electrosurgical cable, and the power consumed by the tissue may be calculated by adding the weighted powers.

The signal processor may calculate the impedance of the tissue at a selected frequency that has the highest weighted magnitude.

In another aspect, the present disclosure features a method for electrosurgical cable compensation. The method includes sensing voltage and current waveforms of electrosurgical energy generated by an electrosurgical generator, passing the sensed voltage and current waveforms having frequencies within a first medium-band range of frequencies including a harmonic frequency, obtaining narrowband phase and magnitude values of at least one frequency of the sensed voltage and current waveforms within the first medium-band range of frequencies, determining medium-band root-mean-square (RMS) voltage and current values based on the passed voltage and current waveforms having frequencies within the first medium-band range of frequencies, estimating an impedance of the tissue based on the narrowband magnitude and phase and the medium-band RMS voltage and current values, and generating a control signal to control the electrosurgical generator to generate energy based on the estimated impedance of the tissue.

The voltage and current waveforms may include harmonic distortion. The first medium-band range of frequencies may include sidebands to the harmonic frequency and/or ringing frequencies.

The method may include passing the sensed voltage and current waveforms having frequencies within a second medium-band range of frequencies including a third harmonic frequency, and obtaining narrowband phase and magnitude values of at least one frequency of the sensed voltage and current waveforms within the second medium-band range of frequencies. The method may include passing the sensed voltage and current waveforms having frequencies within a third medium-band range of frequencies including a fifth harmonic frequency, and obtaining narrowband phase and magnitude values of at least one frequency of the sensed voltage and current waveforms within the third medium-band range of frequencies.

The method may include determining medium-band root-mean-square (RMS) voltage and current values based on the passed voltage and current waveforms having frequencies within the second medium-band range of frequencies, calculating a total RMS voltage value by summing medium-band RMS voltage values, calculating a total RMS current value by summing medium-band RMS current values, selecting frequencies from within the first and second medium-band ranges of frequencies, and calculating weights for the medium-band RMS voltage and current values at the selected frequencies based on the narrowband magnitude values.

A frequency may be selected if a narrowband magnitude at that frequency is greater than or equal to a predetermined value. The weights may be percentages based on ratios between the medium-band RMS voltage values of a medium-band range of frequencies including a selected frequency and the total RMS voltage value, or ratios between the medium-band RMS current values of a medium-band range of frequencies including a selected a frequency and the total RMS current value.

The method may include calculating weighted RMS voltage and current values for the selected frequencies, and calculating the weighted powers based on the weighted RMS voltage and current values to obtain power consumed in the tissue. The power consumed in the tissue may be calculated by adding the weighted powers for the selected frequencies.

The method may include calculating the impedance of the tissue at a selected frequency that has the highest weighted magnitude.

The method may include calculating an average power based on the medium-band RMS voltage and current values to obtain an average power for the first medium-band range of frequencies, and calculating a power loss in the electrosurgical generator based on a known impedance of the electrosurgical generator and the medium-band RMS voltage or current value by subtracting the power loss from the average power. The method may include calculating the narrowband impedance of the tissue at a frequency that has the highest narrowband magnitude, calculating a power consumed in the tissue by subtracting the power loss from the average power, and compensating the impedance of the tissue based on the power consumed in the tissue.

The voltage and current waveforms may include sinusoidal waveforms, square waveforms, rectangular waveforms, triangular waveforms, spiked waveforms, trapezoidal waveforms, and/or sawtooth waveforms. The voltage and current waveforms may include harmonic distortion.

In yet another aspect, the present disclosure features an electrosurgical generator that generates energy to treat tissue via an electrosurgical cable. The electrosurgical generator includes a voltage sensor that senses a voltage waveform of the generated energy, a current sensor that senses a current waveform of the generated energy, a first wideband filter that passes the sensed voltage waveform having at least one frequency within a wide-band range of frequencies including frequencies of interest, a second wideband filter that passes the sensed current waveform having at least one frequency within the wide-band range of frequencies, a plurality of analog-to-digital converters (ADCs) that samples the sensed voltage and current waveforms, a first narrowband filter that obtains narrowband phase and magnitude values of at least one frequency of the sensed voltage waveform within the wide-band range of frequencies, a second narrowband filter that obtains narrowband phase and magnitude values of at least one frequency of the sensed current waveform within the wide-band range of frequencies, and a signal processor. The signal processor determines wideband root-mean-square (RMS) voltage and current values, and an average power based on sample-by-sample products of the sensed voltage and current waveforms filtered by the first and second wideband filters to obtain a wideband RMS power, estimates the impedance of the tissue based on the wide-band RMS voltage and current values and the narrowband magnitude and phase values, calculates RMS voltage and current values at the tissue based on the wideband RMS power and the estimated impedance of the tissue, and generates a control signal to control the electrosurgical generator to generate energy based on the wideband RMS voltage and current values, the average power at the tissue, and the estimated impedance of the tissue.

A power loss in the electrosurgical generator may be calculated based on a known impedance of the electrosurgical generator and the wideband RMS voltage or current value, and the signal processor may calculate power consumed in the tissue by subtracting the power loss from the average power.

The signal processor may calculate the narrowband impedance of the tissue at a single frequency that has the highest narrowband magnitude. The RMS voltage value $V_{rms\_Tissue}$ across the tissue and the RMS current value $I_{rms\_Tissue}$ passing through the tissue may be calculated according to the following equations:

$$V_{rms\_Tissue} = \sqrt{P_{Tissue} \cdot Z_{Tissue}},$$

and $$I_{rms\_Tissue} = \sqrt{\frac{P_{Tissue}}{Z_{Tissue}}},$$

where $P_{Tissue}$ is a power consumed in the tissue and $Z_{Tissue}$ is the narrowband impedance of the tissue at the single frequency.

The voltage and current waveforms may include sinusoidal waveforms, square waveforms, rectangular waveforms, triangular waveforms, spiked waveforms, trapezoidal waveforms, and/or sawtooth waveforms.

The frequencies of interest may include harmonic frequencies. The harmonic frequencies may include a fundamental frequency and a third harmonic frequency. The harmonic frequencies may include a fifth harmonic frequency.

The first and second narrowband filters may be Goertzel filters and the first and second wide-band filters may be bandpass filters.

In still another aspect, the present disclosure features a method for electrosurgical cable compensation. The method includes sensing voltage and current waveforms of electrosurgical energy generated by an electrosurgical generator, passing the sensed voltage and current waveforms having frequencies within a wide-band range of frequencies including frequencies of interest using a wideband filter, sampling the passed voltage and current waveforms, obtaining narrowband phase and magnitude values of at least one frequency of the sensed voltage and current waveforms within the wide-band range of frequencies, determining wideband root-mean-square (RMS) voltage and current values based on the passed voltage and current waveforms having frequencies within the wide-band range of frequencies, determining an average power based on sample-by-sample products of the sensed voltage and current waveforms passed by the wideband filter, estimating an impedance of the tissue based on the wide-band RMS voltage and current values and the narrowband phase and magnitude values, and generating a control signal to control the electrosurgical generator to generate energy based on the estimated impedance, the wideband RMS voltage and current values, and the average power.

The method may include calculating a power loss in the electrosurgical generator based on a known impedance of the electrosurgical generator and the wideband RMS voltage or current value, and calculating a power consumed in the tissue by subtracting the power loss from the average power.

The method may include calculating a narrowband impedance of the tissue at a single frequency that has the highest narrowband magnitude.

The RMS voltage value $V_{rms\_Tissue}$ across the tissue and the RMS current value $I_{rms\_Tissue}$ passing through the tissue may be calculated according to the following equations:

$$V_{rms\_Tissue} = \sqrt{P_{Tissue} \cdot Z_{Tissue}},$$

and

-continued $$I_{rms\_Tissue} = \sqrt{\frac{P_{Tissue}}{Z_{Tissue}}},$$

where $P_{Tissue}$ is a power consumed in the tissue and $Z_{Tissue}$ is the narrowband impedance of the tissue at the single frequency.

The voltage and current waveforms may include sinusoidal waveforms, square waveforms, rectangular waveforms, triangular waveforms, spiked waveforms, trapezoidal waveforms, and/or sawtooth waveforms.

The frequencies of interest may include harmonic frequencies. The harmonic frequencies may include a fundamental frequency and a third harmonic frequency. The harmonic frequencies may include a fifth harmonic frequency.

BRIEF DESCRIPTION OF THE DRAWINGS

Various embodiment of the present disclosure are described with reference to the accompanying drawings wherein.

DETAILED DESCRIPTION

Figure 1:
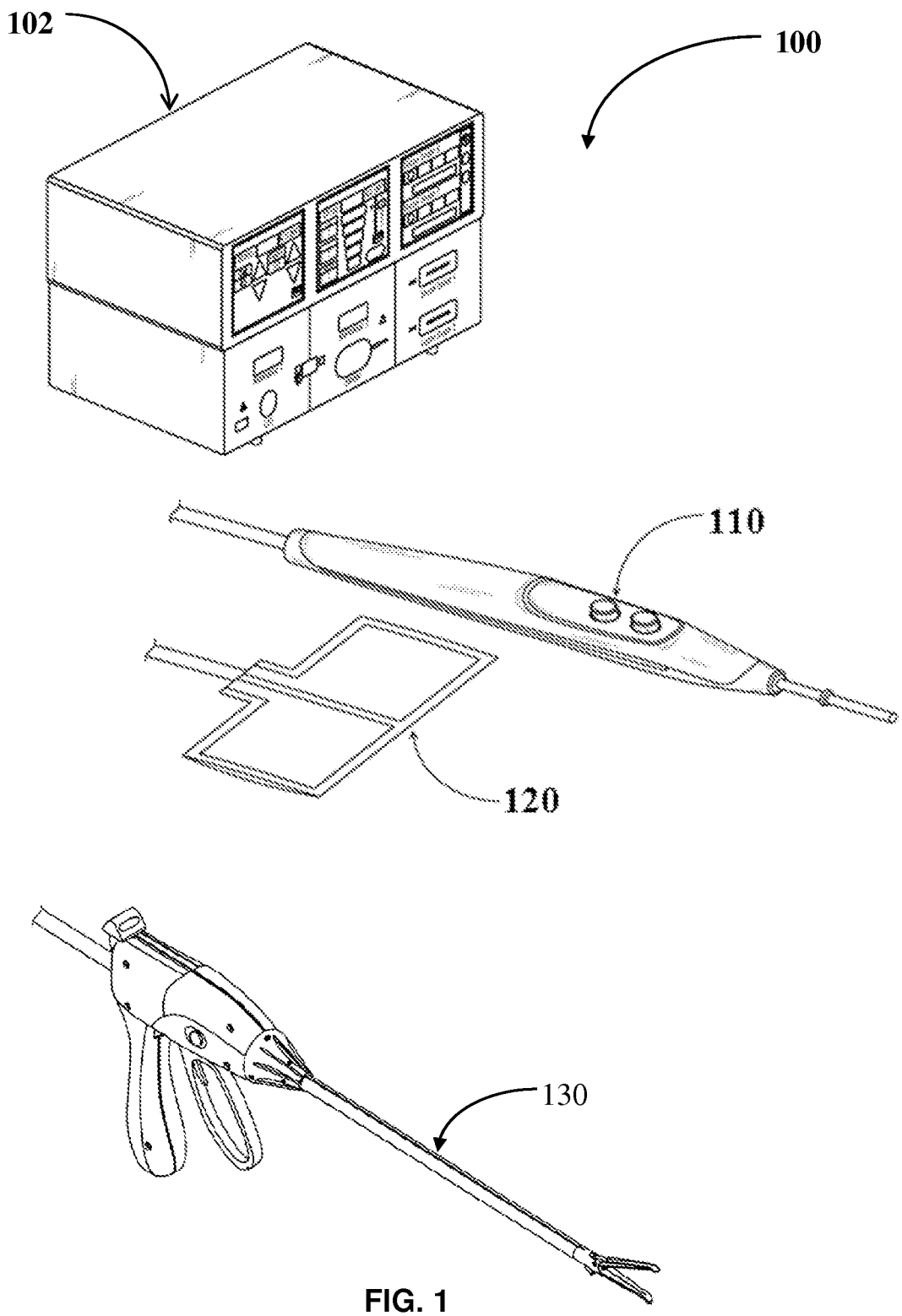
FIG. 1 is an electrosurgical system in accordance with embodiments of the present disclosure.

As described above, an electrosurgical cable in an electrosurgical system creates a circuit network of impedance components between the voltage and current sensors of the electrosurgical system and the tissue being treated, which results in inaccurate power and impedance measurements at the electrosurgical generator. Thus, to more accurately measure power dissipated in and impedance of the tissue being treated, many generators employ compensation algorithms that account for the impedance of the circuit network of the cable assembly. These compensation algorithms involve the measurement and storage of multiple cable parameters, such as series inductance, shunt capacitance, and resistance, which are used as constants in the solutions to the circuit network. These compensation algorithms also involve many mathematical operations, e.g., multiplies and additions, on complex numbers having real and imaginary components.

The electrosurgical systems and methods of the present disclosure increase the accuracy of measurements of the voltage, current, power, and/or impedance of a load, e.g., tissue, by analyzing a range of relevant frequencies. The systems and methods according to the present disclosure may employ different models of the electrosurgical cable assembly for estimating the actual tissue impedance. One model of the cable assembly includes a source impedance having a resistor, a capacitor (e.g., a DC blocking capacitor), and an inductor connected in series with the tissue load and a shunt impedance having a capacitor connected in parallel with the tissue load. The model of the cable assembly may not incorporate the series resistor because the resistance of the series resistor is relatively small compared to the resistance of the tissue load.

Since frequencies other than the fundamental frequency of the generated electrosurgical energy may include a significant amount of energy, multiple frequencies including harmonic frequencies, sidebands, and ringing frequencies are taken into consideration for calculating average power based on sensed current and voltage waveforms. The impedance of the tissue is then calculated at a single frequency which has the highest amount of energy or the highest magnitude to achieve greater signal processing accuracy. Alternatively or additionally, the tissue impedance may be calculated at a single lower frequency, which may be more accurate because tissue impedance calculations are relatively immune to stray parasitic impedances at lower frequencies.

In embodiments, the electrosurgical systems and methods of the present disclosure use complex voltage and current waveforms at multiple frequencies and measured by the current and voltage sensors to calculate the energy lost in the circuit network and actual energy delivered to the tissue being treated. The multiple frequency waveforms generated by the electrosurgical generator are analyzed by narrowband filters, e.g., Fourier transformation, Goertzel, or other frequency transform filters, and then cable compensation is performed for each frequency waveform individually. The results of this cable compensation are then combined to calculate actual current, voltage, power delivered to the tissue being treated, and the tissue impedance.

FIG. 1 illustrates an electrosurgical system 100 in accordance with embodiments of the present disclosure. The electrosurgical system 100 includes an electrosurgical generator 102 which generates electrosurgical energy to treat tissue of a patient. The electrosurgical generator 102 generates an appropriate level of electrosurgical energy based on the selected mode of operation (e.g., cutting, coagulating, ablating, or sealing) and/or the sensed voltage and current waveforms of the generated electrosurgical energy. The electrosurgical system 100 may also include a plurality of output connectors corresponding to a variety of electrosurgical instruments.

The electrosurgical system 100 further includes a monopolar electrosurgical instrument 110 having an electrode for treating tissue of the patient (e.g., an electrosurgical cutting probe or ablation electrode) with a return pad 120. The monopolar electrosurgical instrument 110 can be connected to the electrosurgical generator 102 via one of the plurality of output connectors. The electrosurgical generator 102 may generate electro surgical energy in the form of radio frequency (RF) energy. The electrosurgical energy is supplied to the monopolar electrosurgical instrument 110, which applies the electrosurgical energy to tissue. The electrosurgical energy is returned to the electrosurgical generator 102 through the return pad 120. The return pad 120 provides sufficient contact area with the patient's tissue so as to minimize the risk of tissue damage due to the electrosurgical energy applied to the tissue.

The electrosurgical system 100 also includes a bipolar electrosurgical instrument 130. The bipolar electrosurgical instrument 130 can be connected to the electrosurgical generator 102 via one of the plurality of output connectors. The electrosurgical energy is supplied to one of the two forceps, is applied to tissue, and is returned to the electrosurgical generator 102 through the other forceps.

The electrosurgical generator 102 may be any suitable type of generator and may include a plurality of connectors to accommodate various types of electrosurgical instruments (e.g., monopolar electrosurgical instrument 110 and bipolar electrosurgical instrument 130). The electrosurgical generator 102 may also be configured to operate in a variety of modes, such as ablation, cutting, coagulation, and sealing. The electrosurgical generator 102 may include a switching mechanism (e.g., relays) to switch the supply of RF energy among the connectors to which various electrosurgical instruments may be connected. For example, when the monopolar electrosurgical instrument 110 is connected to the electrosurgical generator 102, the switching mechanism switches the supply of RF energy to the monopolar plug. In embodiments, the electrosurgical generator 102 may be configured to provide RF energy to a plurality instruments simultaneously.

The electrosurgical generator 102 includes a user interface having suitable user controls (e.g., buttons, activators, switches, or touch screens) for providing control parameters to the electrosurgical generator 102. These controls allow the user to adjust parameters of the electrosurgical energy (e.g., the power level or the shape of the output waveform) so that the electrosurgical energy is suitable for a particular surgical procedure (e.g., coagulating, ablating, tissue sealing, or cutting). The electrosurgical instruments 110 and 130 may also include a plurality of user controls. In addition, the electrosurgical generator 102 may include one or more display screens for displaying a variety of information related to the operation of the electrosurgical generator 102 (e.g., intensity settings and treatment complete indicators).

Figure 2:
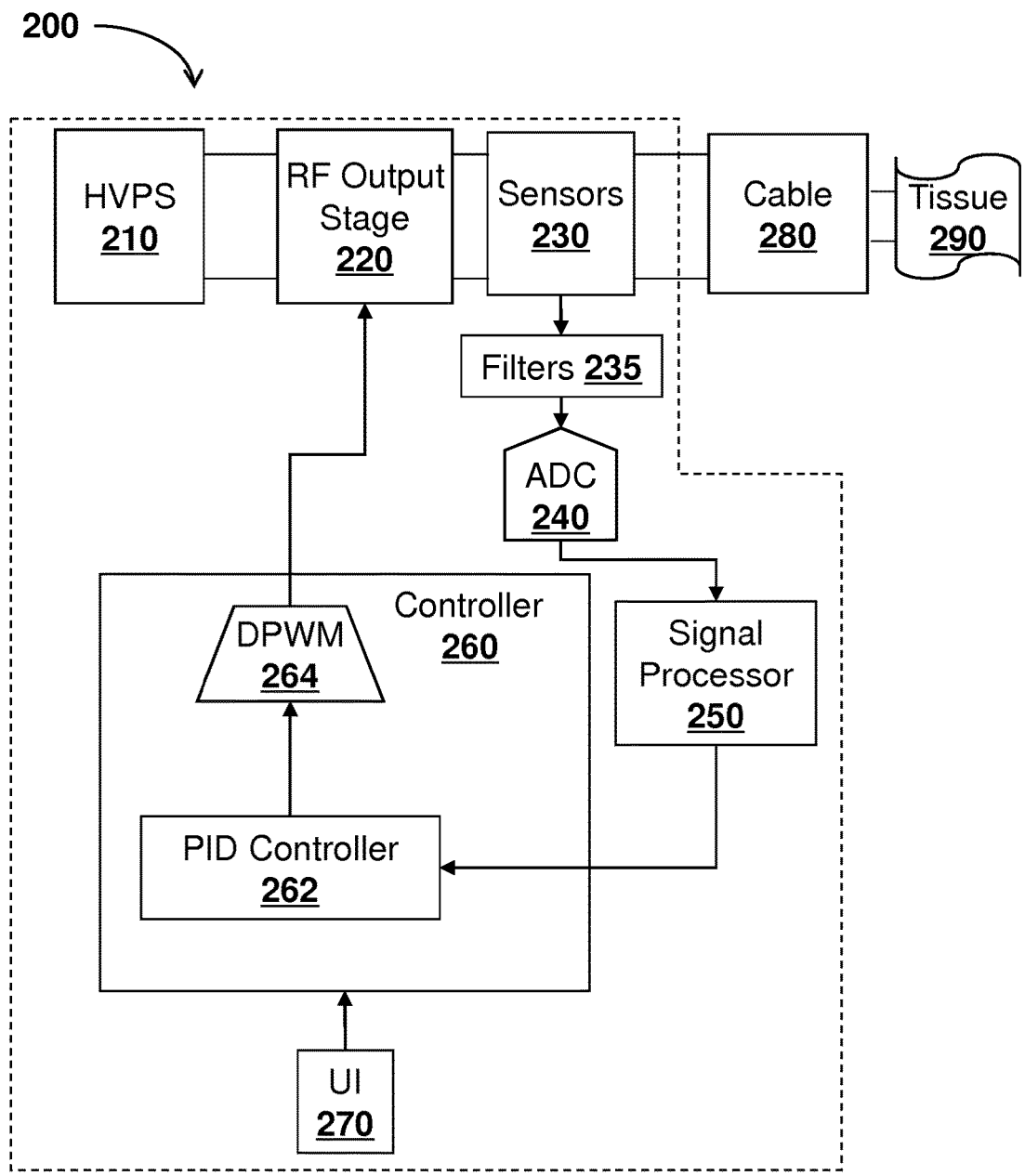
FIG. 2 is a block diagram of circuitry for the electrosurgical system of FIG. 1.

FIG. 2 is a block diagram of the generator circuitry 200 of the electrosurgical generator 102 of FIG. 1 and a cable 280 that delivers electrosurgical energy to treat tissue 290. The generator circuitry 200 includes a high voltage power supply (HVPS) 210, a radio frequency (RF) output stage 220, a plurality of voltage and current sensors 230, filters 235, a plurality of analog-to-digital converters (ADCs) 240, a signal processor 250, which may implement a plurality of filters described in the present disclosure, a controller 260, and a user interface (UI) 270. The generator circuitry 200 is configured to connect to an AC power source, such as a power outlet, which provides AC having a low frequency (e.g., 25 Hz, 50 Hz, or 60 Hz) to the generator circuitry 200. The generator circuitry 200 converts the low frequency AC to higher frequency AC that is suitable for a desired electrosurgical procedure. Specifically, the HVPS 210 converts the AC having a low frequency to high-voltage direct current (DC) and the RF output stage 220 inverts the high-voltage DC to AC having a high frequency that is suitable for an electrosurgical procedure, e.g., 472 kHz.

The appropriate frequency for the electrosurgical energy generated by the generator circuitry 200 may differ based on the electrosurgical procedures and modes of electrosurgery. For example, nerve and muscle stimulations cease at about 100,000 cycles per second (100 kHz) and some electrosurgical procedures can be performed safely at a radio frequency (RF) above 100 kHz. At frequencies over 100 kHz, the electrosurgical energy can pass through a patient to targeted tissue with minimal neuromuscular stimulation. For example, ablation uses a frequency of 472 kHz. Other electrosurgical procedures can be performed at frequencies lower than 100 kHz, e.g., 29.5 kHz or 19.7 kHz, with minimal risk of damaging nerves and muscles. The HVPS 210 and the RF output stage 220 can selectively provide AC signals with various frequencies suitable for various electrosurgical operations. The RF output stage 220 may include a resonant tank circuit that matches the impedance at the RF output stage 220 so that there is maximum or optimum power transfer from the electrosurgical generator 102 to the tissue 290.

The plurality of voltage and current sensors 230 sense the AC voltage and current waveforms generated by the HVPS 210 and the RF output stage 220. In particular, voltage sensors measure voltage across the active and return lines that connect the RF output stage 220 to the cable 280 and the current sensors measure current passing through one of the active and return lines.

The plurality of sensors 230 may include two or more pairs or sets of voltage and current sensors that provide redundant measurements of the voltage and current waveforms. This redundancy ensures the reliability, accuracy, and stability of the voltage and current measurements at the output of the RF output stage 220. In embodiments, the plurality of sensors 230 may include fewer or more sets of voltage and current sensors depending on the application or the design requirements.

The sensed voltage and current waveforms sensed by the plurality of sensors 230 are filtered by filters 235 and sampled by the plurality of ADCs 240 to obtain digital samples of the voltage and current waveforms. The filters 235 may include an anti-aliasing filter and a high-pass filter, which together form a band-pass filter. The plurality of ADCs 240 may sample the sensed voltage and current waveforms at a frequency that is an integer multiple of the frequency of the voltage and current waveforms generated by the RF output stage 220. The number of samples may be a power of two, e.g., 2, 4, 8, 16, 32, or 64 samples per cycle, as the nulls of the filters may fall near the harmonics. Alternatively, the number of samples may not be an even multiple. The sampled current and voltage waveforms are then processed by the signal processor 250 to obtain the root mean square (RMS) voltage and current values, phases, and magnitudes of the sampled current and voltage waveforms, which are provided to the controller 260.

Before the ADCs 240 sample the voltage and current waveforms, a wideband filter may pass a wide range of frequencies of interest. The wideband filter may be a band-pass filter so that low frequencies and high frequencies outside of the frequencies of interest are in the stopband of the wideband filter. In this way, high frequency noise and unwanted low frequencies can be removed before sampling and power computations. The frequencies of interest may fit within the frequency range that the ADCs 240 can handle.

The signal processor 250 may implement a plurality of narrowband filters and a plurality of medium-band filters. The plurality of narrowband filters may provide information regarding the phase difference between the sensed voltage and current waveforms, and the magnitude of the sensed voltage and current waveforms at a single frequency, which may be used to determine the load impedance. The plurality of medium-band filters may filter the voltage and current RF waveforms to calculate an RMS voltage, an RMS current, and an average power over a set of frequencies. The set of frequencies may include the fundamental frequency or harmonics of the RF waveform and its sidebands which are caused by pulse repetition. The narrowband filter is used to pass a narrow range of frequencies, generally a single frequency. The medium-band filter has a wider bandwidth than the narrowband filter and may select a medium range of frequencies. For example, the narrowband filter may have a bandwidth of 10 kHz and the medium-band filter may have a bandwidth of 100 kHz.

Each filter of the plurality of medium-band filters may filter a harmonic frequency, sideband frequencies of the harmonic frequency, and ringing frequencies. Each filter of the plurality of narrowband filters may filter a harmonic frequency or a center frequency of frequencies filtered by a medium-band filter.

The controller 260 includes a proportional-integral-derivative (PID) controller 262 and a digital pulse width modulator (DPWM) 264. In other embodiments, the controller 260 may perform control methods other than or in addition to PID control methods. The PID controller 262 receives the output from the signal processor 250, which may be the estimated average power or impedance of the tissue, and performs a PID control algorithm based on the output from the signal processor 250. The output from the PID controller 262 is provided to the DWPM 264 which generates a control signal to control the output of the RF output stage 220. In particular, the control signal may control the duty cycle so that output power generated by the RF output stage 220 is controlled.

The controller 260 also receives inputs from the UI 270 and generates control signals based on the received inputs. A user may set an electrosurgical operation mode (e.g., cutting, coagulating, ablating, or sealing) and corresponding electrosurgical signal type (e.g., pure sinusoidal, rectangular, sawtooth, pulse, triangular, or blended waveforms). The UI 270 may also allow a user to select a type of electrosurgical procedure (e.g., monopolar or bipolar), or to input desired control parameters for the electrosurgical procedure or the mode.

Figure 3:
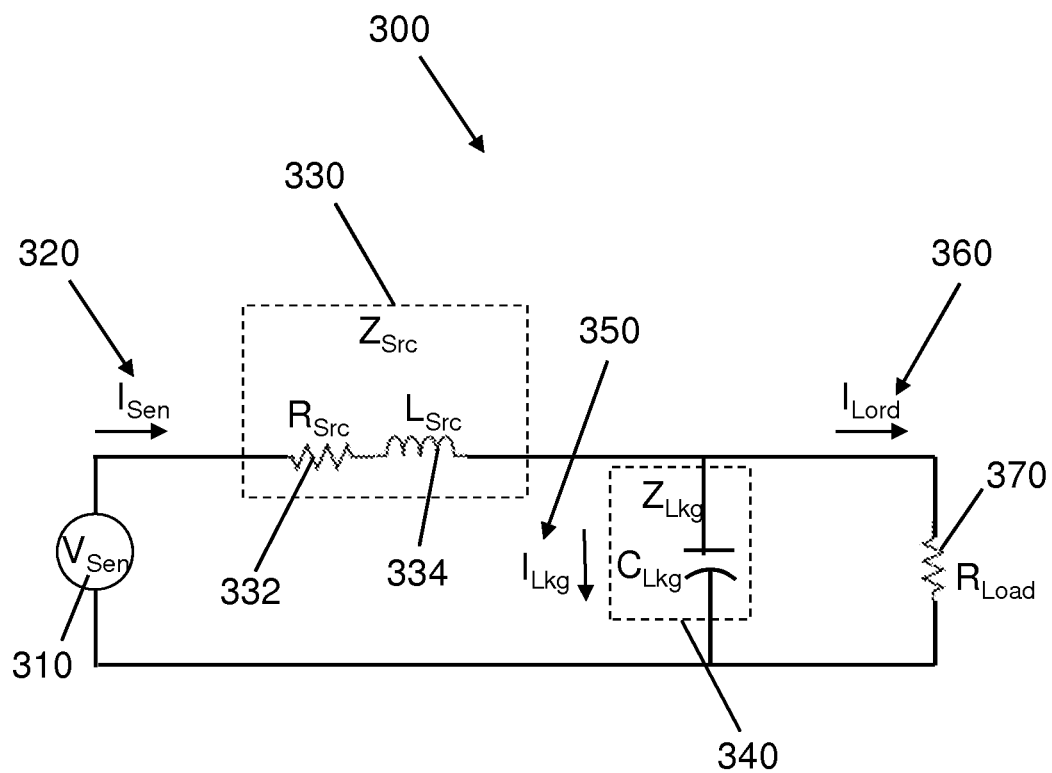
FIG. 3 is a circuit diagram illustrating a model of the electrosurgical cable assembly in accordance with embodiments of the present disclosure.

FIG. 3 is a circuit diagram of a model 300 of the impedance of the cable 280 of FIG. 2. As described above, the generator circuitry 200 delivers electrosurgical energy to the tissue 290 via the cable 280. The plurality of sensors sense voltage $V_{Sen}$ 310 and current $I_{Sen}$ 320. The cable model 300 includes a source impedance $Z_{Src}$ 330 in series with the tissue load resistance $R_{Load}$ 370, which is modeled as a resistor because the tissue impedance is mostly resistive, and a shunt impedance $Z_{Lkg}$ 340 in parallel with the tissue load resistance $R_{Load}$ 370. The source impedance $Z_{Src}$ 330 includes a source resistance $R_{Src}$ 332, a source capacitance $C_{Src}$ (a DC blocking capacitor), which is not shown in FIG. 3, and a source inductor $L_{Src}$ 334 coupled together in series. The shunt impedance $Z_{Lkg}$ 340 includes a leakage capacitance $C_{Lkg}$ 340.

When the current $I_{Sen}$ 320 passes through the source resistance $R_{Src}$ 332, the sensed voltage $V_{Sen}$ 310 drops across the source resistance $R_{Src}$ 332. The source capacitor $C_{Src}$ has an impedance that decreases with increase in frequency. Thus, the source capacitor $C_{Src}$ blocks the DC component of the current $I_{Sen}$ 320 at low frequencies, but represents a small impedance at higher frequencies and thus a small voltage drop. Then, the current $I_{Sen}$ 320 is divided into $I_{Lkg}$ 350 and $I_{Load}$ 360. As a result, the sensed current $I_{Sen}$ 320 is different from the current passing through the tissue load resistance 370 due to leakage current $I_{Lkg}$ 350 through the leakage capacitance $C_{Lkg}$ 340. Also, the sensed voltage $V_{Sen}$ 310 is different from the voltage across the tissue load resistance $R_{Load}$ 370 due to the source resistance $R_{Src}$ 332. Thus, the power calculated from the sensed voltage and current waveforms is different from the actual power delivered to the tissue load resistance $R_{Load}$ 370.

Figure 4A:
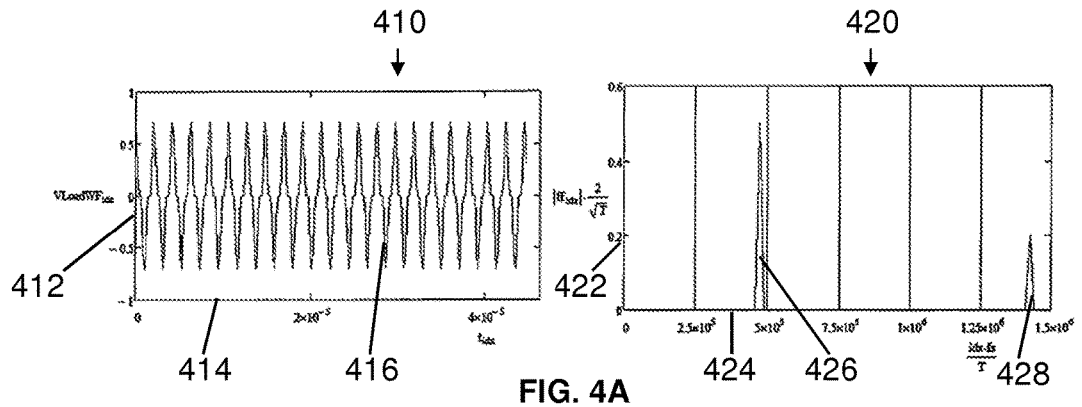
FIGS. 4A-4C are graphical diagrams illustrating the signals generated by the electrosurgical generator of FIG. 2.
Figure 4B:
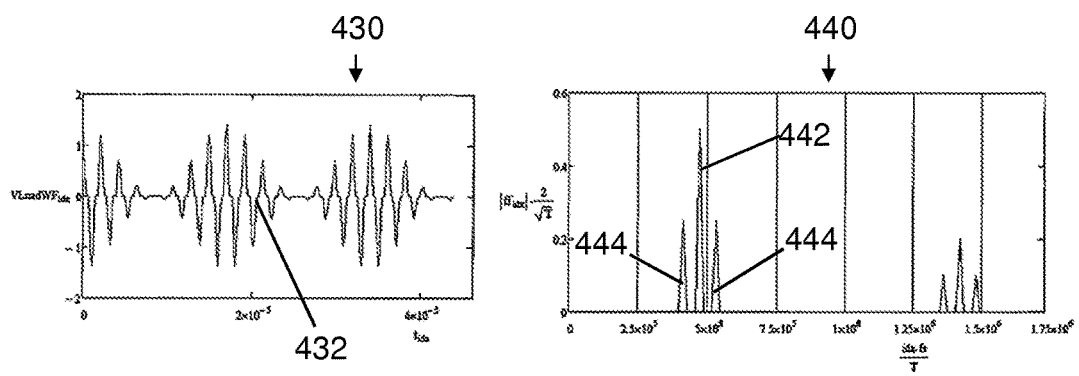
Figure 4C:
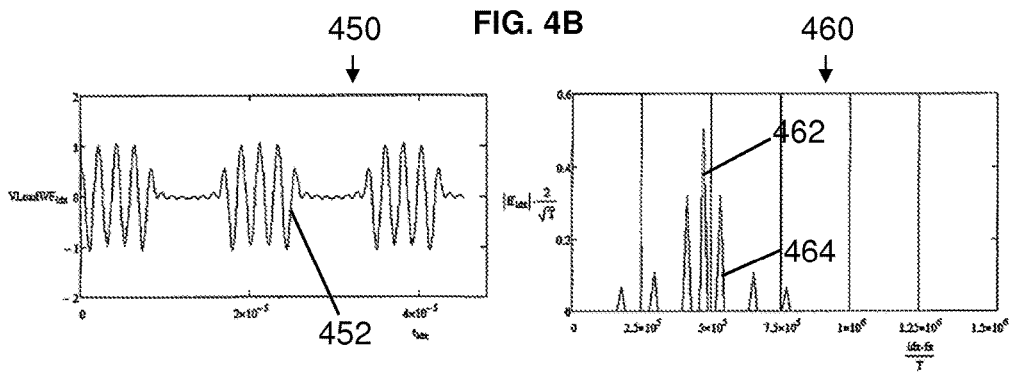

FIGS. 4A-4C illustrate the frequency content of various electrosurgical AC signals generated by electrosurgical generators.

FIG. 4A shows graphs of a continuous signal and its frequency spectrum. The continuous signal is not a pure sinusoid due to harmonic distortion that may introduce a third harmonic frequency or higher harmonic frequencies into the continuous signal. Thus, the continuous signal may includes a fundamental frequency and the third harmonic frequency, as shown, for example, in graph 410, which has two axes: a vertical axis 412 representing the voltage across the tissue being treated and a horizontal axis 414 representing time.

The signal 416 is a sinusoidal signal having a voltage that oscillates between about 0.7 volts and about −0.7 volts with a period of about $2.12 \cdot 10^{-6}$ seconds. Graph 420, in which the vertical axis 422 is the magnitude and the horizontal axis 424 is the frequency in Hertz (Hz), shows the frequency components of the signal 416. The frequency components include the first harmonic or fundamental frequency 426 and the third harmonic frequency 428. The fundamental frequency $f_1$ of the signal 416 is 472 kHz and the third harmonic frequency $f_3$ is 1,416 kHz.

FIG. 4B shows graphs 430 and 440 of a modulated continuous signal and its frequency spectrum. The signal 432 is the continuous signal 416 of FIG. 4A modulated by another sinusoidal signal. The modulating sinusoidal signal has a lower frequency $f_m$ than the fundamental frequency $f_1$ of the continuous signal 416. As shown in the frequency information graph 440, the fundamental frequency $f_1$ 442 is 472 kHz and the modulating frequency $f_m$ appears in the graph 440 as sidebands 444, $f_1+f_m$ and $f_1-f_m$. The third harmonic frequency $f_3$ is also surrounded by sidebands, $f_3+f_m$ and $f_3-f_m$.

FIG. 4C shows graphs of another modulated sinusoidal signal and its frequency spectrum. Graph 450 shows a sinusoidal waveform modulated by a square waveform, resulting in the modulated waveform 452 with no third harmonic distortion in the carrier signal. In general, square waveforms have multiple frequency components. The modulating square waveform includes three frequencies $f_{m1}$, $f_{m2}$, and $f_{m3}$. Thus, as shown in the frequency spectrum graph 460 of FIG. 4C, the modulated waveform 452 includes the fundamental frequency $f_1$ 462 surrounded by sidebands at the frequencies $f_1+f_{m1}$, $f_1-f_{m1}$, $f_1+f_{m2}$, $f_1-f_{m2}$, $f_1+f_{m3}$, and $f_1-f_{m3}$.

In the case where a continuous signal is modulated by a pulse-width modulation (PWM) signal, the continuous signal is turned on for a first portion of a period and is turned off for a second portion of the period. When the continuous signal is turned off, ringing frequencies appear. The ringing frequencies are caused by the parasitic electrical components of the output stage and can ring at the RF output stage's natural frequencies. When the continuous signal is turned off, the ringing frequencies also deliver energy to the load and are defined by the RF output stage design and the load impedance. The ringing frequencies, however, are not related to the fundamental frequency or the third harmonic frequency. Thus, systems and methods of the present disclosure utilize multi-frequency compensation methods even when the continuous signal is turned off.

Figure 5A:
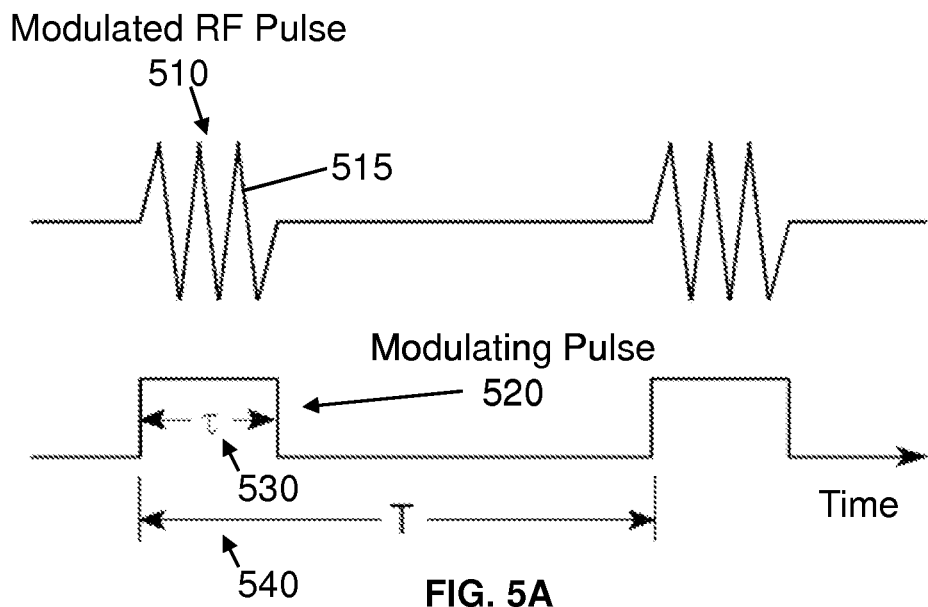
FIGS. 5A and 5B are graphical diagrams illustrating the signals modulated by a modulating pulse.

FIG. 5A illustrates a modulated RF pulse 510 and a modulating pulse in the time domain. The modulated RF pulse 510 is formed by modulating a sinusoidal waveform 515 (not shown) by the modulating pulse 520. Thus, as shown in FIG. 5A, portions of the sinusoidal waveform 515 appear in the modulated RF pulse 510 when the modulating pulse 520 has a first high level and the other portions do not appear when the modulating pulse 520 has a second low level. The modulating pulse 520 has two periods. One of the two periods is a pulse width (PW) $\tau$ 530 during which the modulating pulse has a first high level and the other period is a pulse repetition interval (PRI) T 540 during which the modulating pulse 520 is repeated.

Figure 5B:
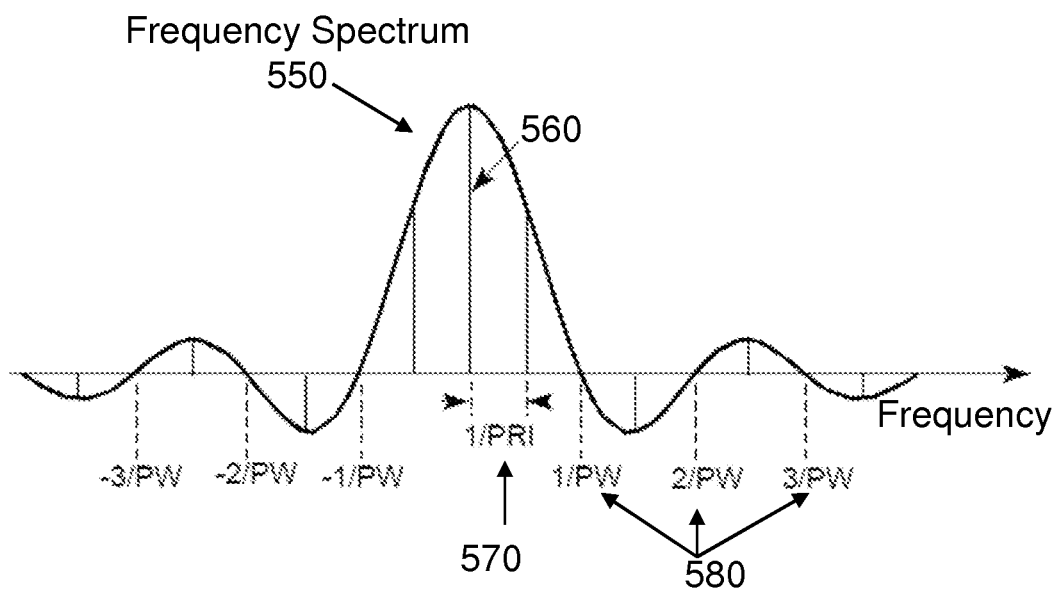

FIG. 5B illustrates the frequency spectrum 550 of the modulated RF pulse 510. The frequency spectrum 550 includes many frequency components, including the center frequency 560, which is the fundamental frequency or the first harmonic frequency of the pre-modulated RF waveform. The main lobe of the frequency spectrum 550, which is centered around the center frequency 560, has a width of two times $1/\tau$ (570) and the other lobes have a width of $1/\tau$ (580). The frequency spectrum 550 shows that the frequency spectrum has zero magnitude every 1/PRI except in the main lobe. This is because the modulating pulse 520 has a 50% duty cycle, meaning that the ratio between the PW $\tau$ 520 and the PRI T 540 is one half. It follows that every third harmonic frequency will have a zero magnitude when the duty cycle is one third or 33.33%.

The magnitude of the main lobe of the frequency spectrum 550 is greater than the magnitude of the other lobes. An absolute value of the magnitudes is the power distributed at the corresponding frequencies. As shown in FIG. 5B, the magnitudes of the other sideband lobes taper off, meaning that power distributed to the sidebands also tapers off. Nevertheless, a significant amount of power is delivered via the sideband frequencies. Thus, the systems and methods of the present disclosure employ a plurality of medium-band filters to measure energy at multiple frequencies.

Figure 6:
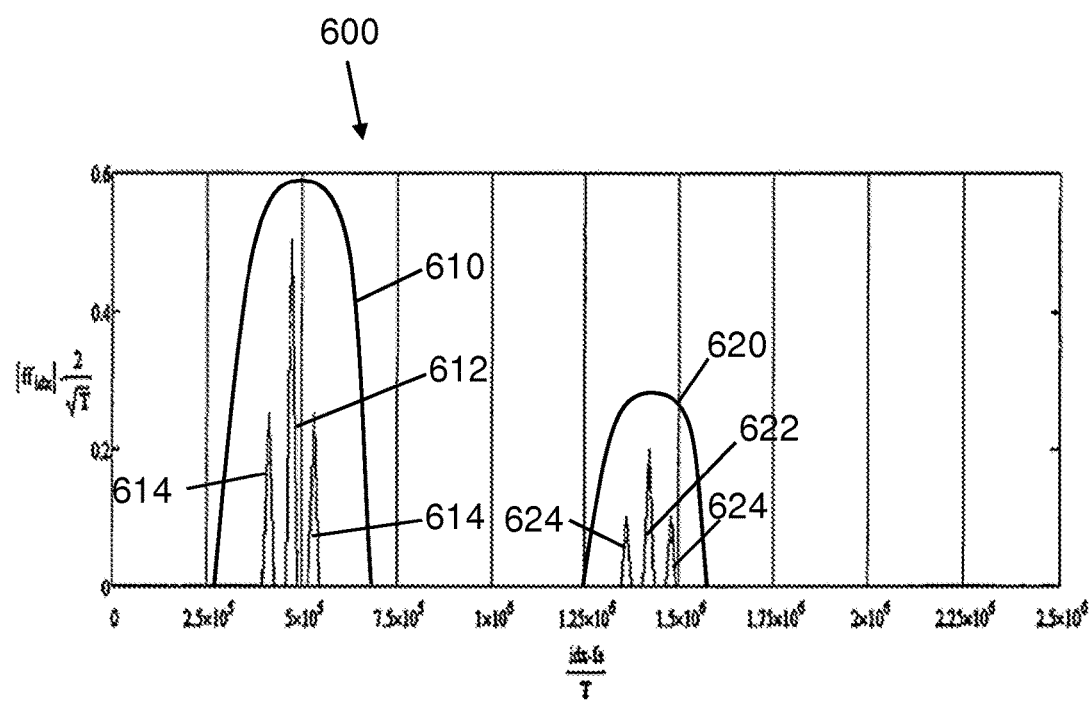
FIG. 6 is a graphical diagram illustrating medium-band filters that pass groups of harmonic frequencies and their sidebands.

FIG. 6 is a graph 600 illustrating medium-band filtering of electrosurgical signals to separate harmonic frequencies from corresponding sideband frequencies so that the harmonic frequencies and the sideband frequencies may be processed separately. The passbands 610 and 620 of the medium-band filters pass a harmonic frequency, e.g., a fundamental or center frequency, and sideband frequencies. More specifically, the passband 610 passes the fundamental frequency 612 and the sideband frequencies 614, and the passband 620 passes the third harmonic frequency and corresponding sideband frequencies 624. Another passband may further pass the fifth harmonic and corresponding sideband frequencies. The wideband filters, as shown in FIG. 2, are used to pass all relevant frequencies shown in FIG. 6, i.e., all frequencies within the range of frequencies of the passbands 610 and 620. The medium-band filters pass a range of frequencies and the narrowband filters pass a center frequency within the range of frequencies.

The electrosurgical signal waveform illustrated in FIG. 6 is modulated by a modulating signal having a 50% duty cycle. If the duty cycle is changed to 33.33%, the plurality of medium-band filters may pass different harmonic frequencies from those passed at the 50% duty cycle. Thus, the duty cycle of the modulating signal determines which harmonics and sideband frequencies are passed. Also, the number of medium-band filters needed is dependent upon the level of accuracy that is needed.

To perform multi-frequency compensation, narrowband root-mean-square (RMS) measurements are taken for each of the fundamental frequency and relevant harmonics. These measurements are combined to determine the total RMS voltage, the RMS current, and the average power at the load. Then, the tissue impedance is calculated at a single frequency, e.g., the fundamental frequency or a harmonic frequency.

As shown in FIGS. 4A-6, the sidebands are symmetric around a center frequency. Due to this symmetry, impedance components of the cable cancel out. For example, as shown in FIG. 4C, there are six sidebands 464 around the center frequency $f_1$ 462, namely, $f_1+f_{m1}$, $f_1-f_{m1}$, $f_1+f_{m2}$, $f_1-f_{m2}$, $f_1+f_{m3}$, and $f_1-f_{m3}$. The first sideband frequency $f_1+f_{m1}$ is higher than the fundamental frequency. Thus, energy passes through the parasitic capacitance at the first sideband frequency $f_1+f_{m1}$ more easily than at the fundamental frequency $f_1$. The second sideband frequency $f_1-f_{m1}$ is lower than the fundamental frequency $f_1$. Thus, less energy passes through the parasitic capacitance at the second sideband frequency $f_1-f_{m1}$ than at the fundamental frequency $f_1$. The fact that the first and second sidebands are spaced equally on either side of the fundamental frequency $f_1$ suggests that the total energy which passes through the parasitic capacitance at the first and second sideband frequencies averages out as if the total energy passing through the parasitic capacitance is at the fundamental frequency $f_1$.

The third and fourth sideband frequencies $f_1+f_{m2}$ and $f_1-f_{m2}$, and the fifth and sixth sideband frequencies $f_1+f_{m3}$ and $f_1-f_{m3}$, produce the same results as the first and second sideband frequencies. Thus, the total energy passing through the parasitic capacitance at the third and the fourth sideband frequencies average out as if the total energy passes through the parasitic capacitance at the fundamental frequency. Similarly, the total energy passing through the parasitic capacitance at the fifth and sixth sideband frequencies average out as if the total energy passes through the parasitic capacitance at the fundamental frequency. Consequently, the aggregate total energy passing through the parasitic capacitance at all sideband frequencies can be considered to pass through the parasitic capacitance at the fundamental frequency. For these reasons, compensation is performed at a single frequency by using the amplitude of the medium-band filter, which captures energy at the fundamental frequency and all its sidebands.

The single frequency used for load impedance calculations may be selected from among the fundamental or harmonic frequencies when the magnitude of the electrosurgical signal at the single frequency is higher than the magnitude of the electrosurgical signal at other frequencies.

Figure 7A:
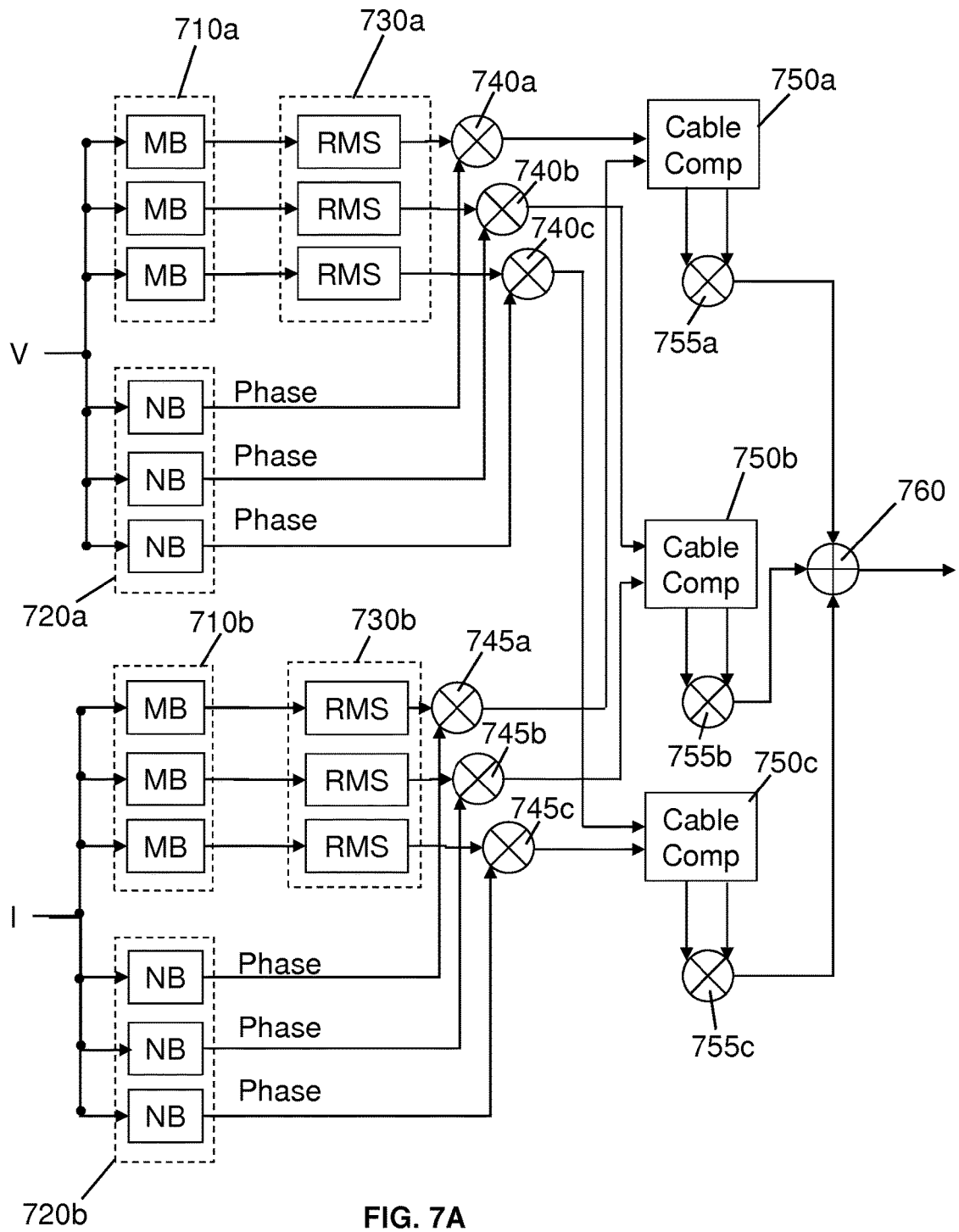
FIG. 7A is a block diagram of circuitry for determining the power of an electrosurgical signal.

FIG. 7 shows a block diagram of a signal processing circuit that calculates phases and magnitudes of voltage and current waveforms and RMS powers via medium-band and narrowband filters. The signal processing circuit includes medium-band filters 710a for the sensed voltage waveform and medium-band filters 710b for the sensed current waveform, narrowband filters 720a and 720b. The signal processing circuit also includes RMS calculators 730a and 730b, multipliers 740a-740c, 745a-745c, cable compensators 750a-750c, multipliers 755a-755c, and an adder 760 for calculating the total power dissipated in the tissue being treated. The signal processing circuit may be implemented by the signal processor 250 of FIG. 2 or by a combination of the signal processor 250 and the controller 260.

The sensed voltage and current waveforms are filtered by the plurality of medium-band filters 710a and 710b, respectively. As described above with respect to FIGS. 4A-6, each of the plurality of medium-band filters 710a and 710b passes a harmonic frequency and corresponding sidebands or ringing frequencies in which energy is present. For example, one medium-band filter may have a passband (e.g., passband 610 of FIG. 6) that passes the fundamental frequency (e.g., frequency 612) and its sidebands (e.g., sidebands 614) and another medium-band filter may have a passband (e.g., passband 620) that passes the third harmonic frequency (e.g., third harmonic frequency 622) and its sidebands (e.g., sidebands 624), or a single wideband filter may pass all the significant harmonics and sidebands.

The plurality of medium-band filters 710a and 710b are connected to a respective plurality of RMS calculators 730a and 730b so that voltage and current waveforms filtered by the plurality of medium-band filters 710a and 710b are provided to the RMS calculators 730a and 730b. The RMS calculators 730a and 730b calculate RMS voltage and current values and provide them to corresponding multipliers 740a-740c and 745a-745c. The RMS voltage and current values may be calculated in quadrature according to the following equations:

$$I_{RMS\_n} = \sqrt{\frac{\sum_{k=1}^{n} I_k^2}{n}}, \text{ and} \tag{1}$$

$$V_{RMS\_n} = \sqrt{\frac{\sum_{k=1}^{n} V_k^2}{n}}, \tag{2}$$

where $I_{RMS\_n}$ is the RMS current value at each of a plurality of frequencies, $V_{RMS\_n}$ is the RMS voltage value at each of a plurality of frequencies, $I_k$ are the current values output from the medium-band filters 710b at each of a plurality of frequencies, $V_k$ are voltage values output from the medium-band filters 710a at each of a plurality of frequencies, and n is the number of voltage or current samples for RMS calculation.

The sensed current and voltage waveforms are also provided to a plurality of narrowband filters 720a and 720b. The plurality of narrowband filters 720a filter the sensed voltage waveform and the plurality of narrowband filters 720b filter the sensed current waveform to obtain phase and magnitude information for the sensed current and voltage waveforms at selected frequencies of the narrowband filters 720a and 720b. Narrowband filters 720a and 720b are tuned to a center frequency, a fundamental frequency, or a harmonic frequency that is among the plurality of frequencies filtered by the corresponding medium-band filters 710a and 710b. The narrowband filters 720a and 720b may be windowed Goertzel filters having a window size that is an integer multiple of the period of the current and voltage waveforms.

The number of medium-band filters 710a and 710b and narrowband filters 720a and 720b is predetermined based on the knowledge of the harmonics, sidebands, and expected ringing frequencies associated with the signal generated by the electrosurgical generator. For example, as illustrated in FIG. 7, the number of medium-band filters 710a and 710b and narrowband filters 720a and 720b is three so that the fundamental frequency, the third harmonic frequency, and the fifth harmonic frequency are passed. The number of medium-band filters 710a and 710b and narrowband filters 720a and 720b may also be increased or decreased depending on the desired level of accuracy.

Each multiplier of the plurality of multipliers 740a-740c multiplies an RMS voltage and a corresponding phase to convert a voltage in rectangular form, i.e., the real and imaginary parts, into polar form, i.e., magnitude and phase, for each group of a harmonic frequency and corresponding sidebands. The phase between the voltage and current may be determined from the narrowband filter output, such that the phase shift between the voltage and current in reference to the voltage is the difference between the phase of the voltage waveform and the phase of the current waveform in radians. Similarly, each multiplier among the plurality of multipliers 745a-745c multiplies an RMS current and a corresponding phase to calculate a current value in rectangular form for each group of a harmonic frequency and corresponding sidebands. These operations are represented by the following equations:

$$V_{RMS} = V_{RMS\_n} \times e^{j\phi_{v\_n}} = V_{RMS\_n} \cdot \cos\phi_{v\_n} + jV_{RMS\_n} \cdot \sin\phi_{v\_n}, \text{ and} \tag{3}$$

$$I_{RMS} = I_{RMS\_n} \times e^{j\phi_{I\_n}} = I_{RMS\_n} \cdot \cos\phi_{I\_n} + jI_{RMS\_n} \cdot \sin\phi_{I\_n}, \tag{4}$$

where $V_{RMS}$ is the RMS voltage in rectangular form, $V_{RMS\_n}$ is the magnitude of the RMS voltage $V_{RMS}$, $\phi_{V\_n}$ is the phase of the voltage at a single frequency (e.g., the fundamental or harmonic frequency), $I_{RMS}$ is the RMS current, $I_{RMS\_n}$ is the magnitude of the RMS current $I_{RMS}$, $\phi_{I\_n}$ is the phase of the current at a single frequency (e.g., the fundamental or harmonic frequency). In other words, the output from the multipliers 740a-740c and 745a-745c are estimated RMS voltages and currents generated by the electrosurgical generator to be delivered to the tissue via a cable for each group of frequencies in rectangular or complex form.

The complex RMS voltage from the multiplier 740a and the complex RMS current from the multiplier 745a are provided to cable compensator 750a that compensates for the parasitics of the cable. In the same way, the complex RMS voltage from the multiplier 740b and the complex current from the multiplier 745b are provided to the cable compensator 750b, and the complex RMS voltage from the multiplier 740c and the complex RMS current from the multiplier 745c are provided to the cable compensator 750c. The cable compensators 750a-750c perform cable compensation using a basic model of the cable and a two-port network system that is shown in FIG. 7B.

Figure 7B:
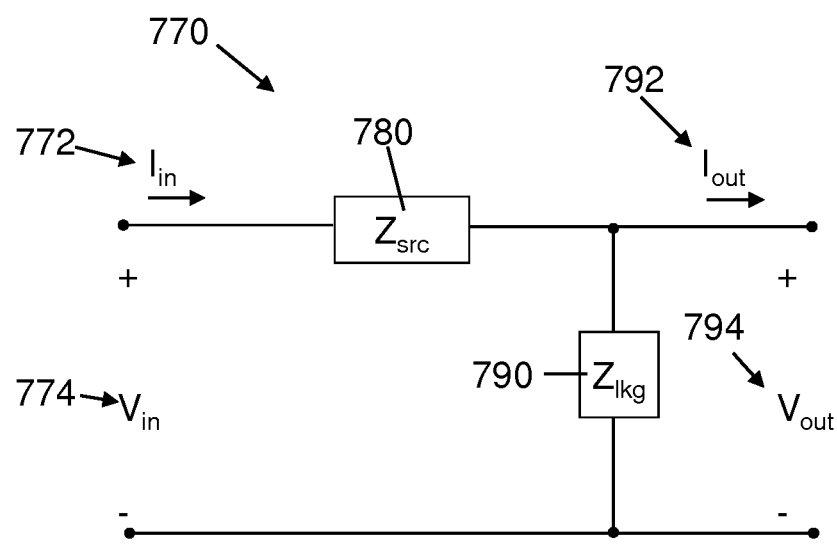
FIG. 7B is a circuit diagram illustrating a two-port network model of the electrosurgical cable assembly in accordance with an embodiment of the present disclosure.

FIG. 7B shows a basic model 770 of the cable that includes a source impedance $Z_{src}$ 780 and a shunt impedance $Z_{lkg}$ 790. The source impedance $Z_{src}$ 780 includes resistive and inductive components of the cable and the shunt impedance $Z_{lkg}$ 790 includes a capacitive component of the cable.

FIG. 7B also shows a two-port network system for the basic model 770 of the cable. The two-port network system includes two inputs and two outputs. The two inputs are voltage $V_{in}$ 774 and current 772, and the two outputs are voltage $V_{out}$ 794 and current $I_{out}$ 792. Voltage $V_{in}$ 774 represents the complex RMS voltage which is generated by the electrosurgical generator and current 772 represents the complex RMS current which is generated by the electrosurgical generator. Voltage $V_{out}$ 794 represents the complex RMS voltage across the tissue and $I_{out}$ 792 represents the complex RMS current passing through the tissue.

The relationship between the two inputs and the two outputs may be described by a system of the following two linear equations:

$$V_{out} = V_{in} - I_{in} \cdot Z_{src}, \text{ and} \quad (5)$$

$$I_{out} = -\frac{V_{in}}{Z_{lkg}} + \frac{Z_{src} + Z_{lkg}}{Z_{lkg}} \cdot I_{in}. \quad (6)$$

The system of two linear equations can be expressed by the following matrix:

$$\begin{bmatrix} V_{out} \\ I_{out} \end{bmatrix} = \begin{bmatrix} A_{11} & A_{12} \\ A_{21} & A_{22} \end{bmatrix} \begin{bmatrix} V_{in} \\ I_{in} \end{bmatrix}, \quad (7)$$

where $A_{11}$ is 1, $A_{12}$ is $-Z_{src}$, $A_{21}$ is $$-\frac{1}{Z_{lkg}},$$

and $A_{22}$ is $$\frac{Z_{src} + Z_{lkg}}{Z_{lkg}}.$$

The complex RMS voltage and current generated by an electrosurgical generator may be calculated by using equation (7) when the parameters of the cable are known.

The cable compensators 750a-750c compensate for the parasitics of the cable to obtain the complex RMS voltage and current at the fundamental or harmonic frequency at the tissue. The two outputs of the cable compensator 750a are provided to the multiplier 755a, which multiplies the compensated complex RMS voltage and current at the tissue to obtain the power dissipated in the tissue. This operation may be expressed by the following equations:

$$P_{comp} = V_{comp} \times I_{Comp}^* \quad (8)$$

$$= V_{comp} \times I_{Comp}((\cos\varphi_V \cos\varphi_I + \sin\varphi_V \sin\varphi_I) +$$

$$j(\cos\varphi_V \sin\varphi_I - \cos\varphi_I \sin\varphi_V)) \quad (9)$$

$$= V_{comp} \times I_{Comp}(\cos(\varphi_V - \varphi_I) + j\sin(\varphi_V - \varphi_I)), \quad (10)$$

where $P_{Comp}$ is the power delivered to the tissue at a harmonic frequency, $I_{Comp}^*$ is a complex conjugate of $I_{Comp}$, which is the cable-compensated complex RMS current, $V_{Comp}$ is the cable-compensated complex RMS voltage, $\phi_V$ is the phase of $V_{Comp}$, and $\phi_I$ is the phase of $I_{Comp}$. Since the tissue is mostly resistive, the real part of $P_{Comp}$ is the power dissipated in the tissue. Multipliers 755b and 755c also calculate the power delivered to the tissue at two harmonic frequencies. For example, multiplier 755a may calculate power at the fundamental frequency, multiplier 755b may calculate power at the third harmonic frequency, and multiplier 755c may calculate power at the fifth harmonic frequency.

The multipliers 755a-755c provide their outputs to the adder 760, which adds the outputs together. The result of the adder 760 is an estimate of the total power or average power dissipated in the tissue for all fundamental and harmonic frequencies. More specifically, the real part of the output from the adder 760 is the power dissipated in the tissue.

For the signal processing circuit shown in FIG. 7, the predetermined harmonic frequencies for calculating the total power delivered to the tissue are the fundamental frequency, the third harmonic frequency, and the fifth harmonic frequency. In embodiments, the signal processing circuit of FIG. 7 may be modified to use more or less groups of frequencies by adding or subtracting filters and multipliers to the filters 710a-b, 720a-b, 730a-b and the multipliers 740a-c, 745a-c, and 755a-c.

The signal processing circuit of FIG. 7 also calculates the tissue impedance according to the following equation:

$$Z_{Tissue} = \frac{V_{Comp}}{I_{Comp}}, \quad (11)$$

where $Z_{Tissue}$ is the tissue impedance, which is mostly resistive and the real part of $Z_{Tissue}$ is an estimate of the tissue resistance. The signal processing circuit of FIG. 7 determines currents and voltages for multiple harmonics. Thus, the signal processing circuit of FIG. 7 may calculate the tissue impedance for any harmonic frequency. The signal processing circuit of FIG. 7 may calculate a tissue impedance value for the fundamental frequency. Alternatively, the signal processing circuit of FIG. 7 may calculate a tissue impedance value for a harmonic frequency that has the highest magnitude.

In embodiments, as shown in equation (10), the signal processing circuit of FIG. 7 may use a phase shift or phase difference between the phase of the voltage waveform and the phase of the current waveform. Then, the power dissipated in the tissue may be calculated by multiplying $V_{RMS\_Comp}$, $I_{RMS\_Comp}$, and a cosine value of the phase shift as follows:

$$P_{Tissue} = V_{RMS\_Comp} \times I_{RMS\_Comp} \cdot \cos(\phi_V - \phi_I), \quad (12)$$

where $V_{RMS\_Comp}$ is the magnitude of the cable-compensated complex RMS voltage $V_{Comp}$ and $I_{RMS\_Comp}$ is the magnitude of the cable-compensated complex RMS current $I_{Comp}$. By doing this, three complex multiplications are reduced to one real number subtraction and two real number multiplications.

Further, the tissue impedance is also calculated by the following:

$$Z_{Tissue} = \frac{V_{RMS\_Comp}}{I_{RMS\_Comp}} \cos(\varphi_V - \varphi_I). \quad (13)$$

Equation (13) only includes real number calculations and does not include the additional step of taking a real part of the impedance as compared to the equation (10). In this way, computational efficiency can be substantially increased.

Figure 8:
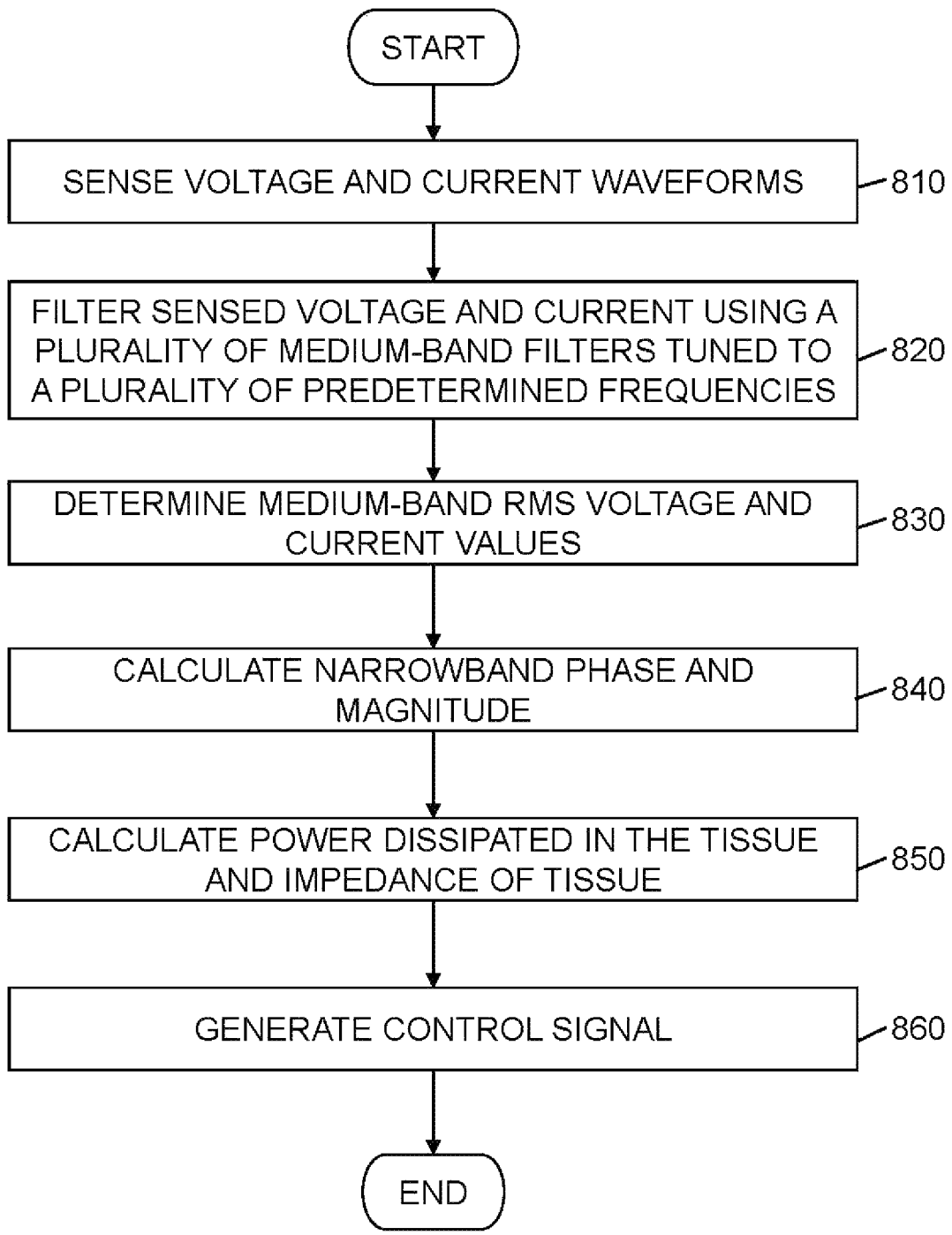
FIG. 8 is a flow diagram of a method for compensating for the impedance of an electrosurgical cable according to embodiments of the present disclosure.

FIG. 8 is a flow chart illustrating a method for compensating for the impedance of an electrosurgical cable according to embodiments of the present disclosure. This method uses a plurality of medium-band filters to calculate RMS power information and a plurality of narrowband filters to calculate phase and magnitude information.

In step 810, sensors sense voltage and current waveforms generated by an electrosurgical generator. In step 820, a plurality of medium-band filters tuned to a respective plurality of groups of frequencies and a plurality of narrowband filters tuned to respective center frequencies in the respective plurality of groups of frequencies filter the sensed voltage and current waveforms. Each group of a plurality of frequencies includes a harmonic frequency and its sidebands. Each group is predetermined based on knowledge of the type of electrosurgical operations and related types of voltage and current waveforms. The generated voltage and current waveforms have a frequency suitable for treating tissue and a type of signal, e.g., a sinusoidal, sawtooth, rectangular, triangular, square, pulse, or any blended waveform. Each medium-band filter passes a harmonic frequency and its sidebands, and each corresponding narrowband filter passes the fundamental frequency, the harmonic frequency, or the center frequency.

In step 830, the RMS calculators 730a and 730b of FIG. 7 calculate medium-band RMS voltage and current values in quadrature according to equations (1) and (2) above. In step 840, the plurality of narrowband filters output phase and magnitude information for each of the harmonic frequencies of the sensed voltage and current waveforms. In step 850, the power dissipated in the tissue is calculated according to either equation (10) or (12) and the tissue impedance is calculated according to either equation (11) or (13).

In step 860, a controller generates a control signal based on the power, the tissue impedance, the RMS voltage, or the RMS current. Generally, electrosurgical generators have a power profile or impedance profile for an electrosurgical operation. Total power dissipated in tissue being treated may be compared to the power profile and the controller generates a control signal to control the level of power generated by the electrosurgical generator. If tissue impedance is calculated, the tissue impedance is compared to the impedance profile and the controller generates a control signal to control the generator output based on the comparison.

Figure 9:
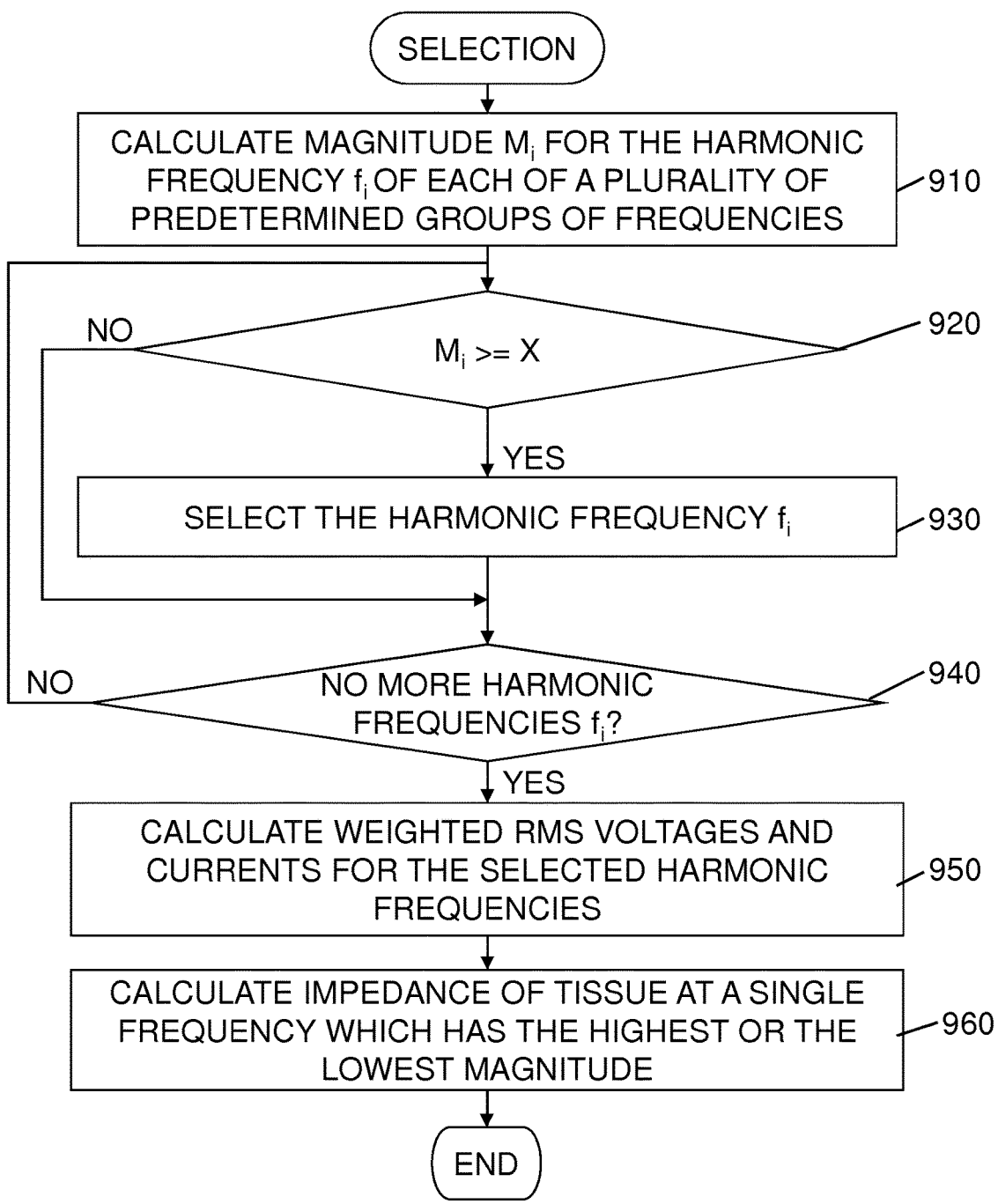
FIG. 9 is a flow diagram of a method for determining power dissipated in tissue at multiple frequencies and determining the tissue impedance at a single frequency according to embodiments of the present disclosure.

FIG. 9 is a flow diagram illustrating the use of weights to estimate the power, the RMS voltage, and the RMS current delivered to the tissue being treated. Step 910 includes steps 810-840 of FIG. 8 for a plurality of frequencies. The frequency $f_i$ represents one or more frequencies among the plurality of predetermined frequencies, e.g., harmonic frequencies, ringing frequencies, or the fundamental frequency, and $M_i$ represents magnitude values for the corresponding frequencies $f_i$. In step 910, a magnitude value $M_i$ is calculated for the frequency $f_i$, which is a frequency among the plurality of predetermined frequencies.

In step 920, the magnitude $M_i$ is compared to a predetermined threshold value X. If the magnitude $M_i$ is greater than or equal to the threshold value X, step 930 is performed. If the magnitude $M_i$ is not greater than or equal to the threshold value X, step 930 is skipped and step 940 is performed. Step 940 checks whether there are any further harmonic frequencies to be checked. If there is another frequency to be check, the method returns to step 920 until every harmonic frequency is checked. In step 920, magnitude $M_i$ may be a magnitude obtained by a plurality of narrowband filters and may be the RMS voltage, the RMS current, or the calculated power. As an alternative, the RMS voltage or current obtained from the plurality of bandpass filters can be compared to a threshold value to select a frequency. In other words, a frequency can be selected when both or either one of an RMS voltage value and an RMS current value of a harmonic frequency and its sidebands are greater than or equal to a threshold value. The threshold value may be a numerical value or a percentage value of the total magnitude.

The frequencies may be selected by expressing the RMS voltage and current values as a percentage value of the total energy in the selected frequencies, in quadrature or in straight percentage, and comparing the resulting percentage values to a percentage threshold. A percentage value in quadrature is calculated for the RMS voltage and current values as follows:

$$V_{QPercentage_i} = \sqrt{\frac{V_i^2}{\sum_{j=1}^{n} V_j^2}} \cdot 100, \text{ and} \qquad (14)$$

$$I_{QPercentage_i} = \sqrt{\frac{I_i^2}{\sum_{j=1}^{n} I_j^2}} \cdot 100, \qquad (15)$$

where $V_{QPercentage_i}$ is a percentage in quadrature of the i-th RMS voltage value, $V_i$ is the i-th RMS voltage value $$\sum_{j=1}^{n} V_j^2$$

is sum of the squares of all RMS voltage values, $I_{Qpercentage_i}$ is a percentage in quadrature of i-th RMS current value, $I_i$ is the i-th RMS current value $$\sum_{j=1}^{n} I_j^2$$

is the sum of the squares of all RMS current values, and n is the number of selected frequencies. A percentage value in straight percentage is calculated for RMS voltage and current values as follows:

$$V_{Percentage_i} = \frac{V_i}{\sum_{j=1}^{n} V_j} \cdot 100, \text{ and} \qquad (16)$$

$$I_{Percentage_i} = \frac{I_i}{\sum_{j=1}^{n} I_j} \cdot 100, \qquad (17)$$

where $V_{Percentage_i}$ is a percentage in straight percentage of the i-th RMS voltage value, $$\sum_{j=1}^{n} V_j$$

is sum of all RMS voltage values, $I_{Percentage_i}$ is a percentage in straight percentage of the i-th RMS current value, $$\sum_{j=1}^{n} I_j$$

is the sum of all RMS current values. The difference between the percentage values in straight percentage and the percentage values in quadrature is that the quadrature percentage tends to enhance differences and thus may be suitable for separating frequencies.

In step 930, when a magnitude $M_i$ of a frequency $f_i$ is greater than or equal to a threshold value X, the frequency $f_i$ is selected. In step 940, when there are no other frequency components, step 950 is performed. In step 950, a weight for the magnitude of each selected frequency is calculated. A weight can be a percentage value in quadrature or in straight percentage. A weighted RMS voltage is calculated by multiplying the weight by the corresponding total wideband RMS voltage and a weighted RMS current is calculated by multiplying a weight by the corresponding total wideband RMS current. Frequencies that are not selected have zero weight, meaning that the frequencies have no RMS voltage, RMS current, and power. In this way, weighted multi-frequency cable compensation is performed on the frequencies that have sufficient energy. Results of the weighted multi-frequency cable compensation are estimates of the total RMS voltage, RMS current, and power delivered to the tissue being treated.

In step 960, the tissue impedance is calculated based on a single frequency. The single frequency may be selected based on the magnitude and frequency of the RF waveform. For example, the single frequency may be selected so as to achieve a high magnitude of the RF waveform at a low frequency. As another example, the single frequency may be selected so as to achieve a high magnitude of the RF waveform at a frequency other than a low frequency, such as a high frequency. If a low frequency is selected, the tissue impedance calculation is performed by using equation (11) or (13) with the calculated phase information. A low frequency may be selected because low frequencies may be more accurate. There is less noise at low frequencies than at high frequencies. On the other hand, a high frequency may be selected because high frequencies have more signal with which to work and signal processing or quantization issues are less problematic. Thus, a sufficiently low frequency may be selected so that the magnitude of the RF waveform is sufficiently high. The calculated tissue impedance is used for generating a control signal to control a level of output power from an electrosurgical generator.

Figure 10:
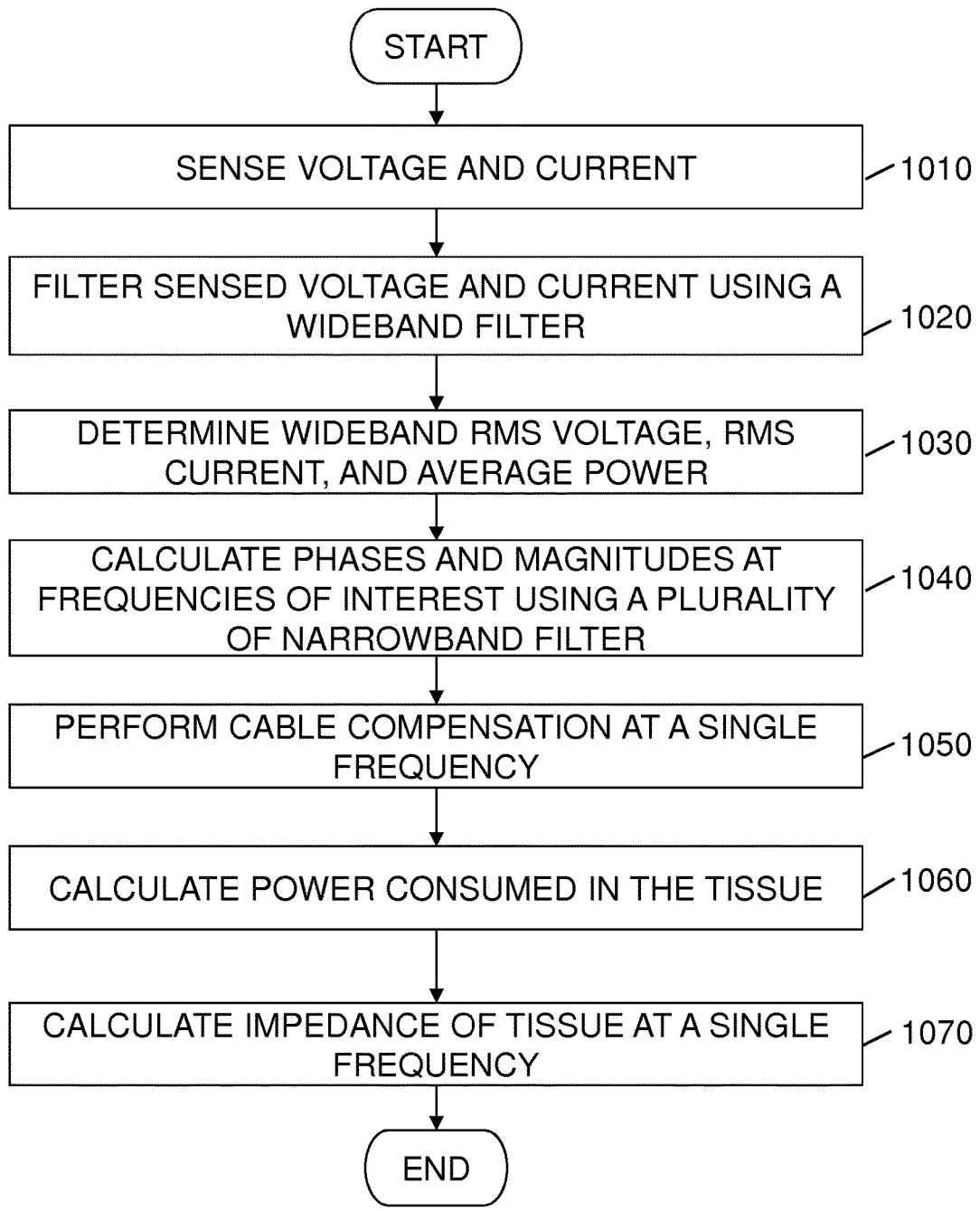
FIG. 10 is a flow diagram of a method for determining the impedance of tissue based on the power consumed in the generator according to other embodiments of the present disclosure.

FIG. 10 is a flow chart of a method for calculating the power, the RMS voltage, and the RMS current at the tissue by compensating for power loss in an electrosurgical generator in accordance with another embodiment of the present disclosure. This method uses the cable model illustrated in FIG. 7B. Generally, power is dissipated in resistive elements of the circuit. Thus, the power generated by the electrosurgical generator is a sum of the power consumed by the source resistance $R_{src}$ 332 and the power consumed by the load resistance $R_{load}$ 370. Thus, the power consumed in the tissue being treated can be calculated by subtracting the power consumed by the source resistance $R_{src}$ 332 from the power generated by the electrosurgical generator.

In step 1010, the plurality of sensors sense the voltage and current waveforms generated by the electrosurgical generator. In step 1020, the sensed voltage and current waveforms are filtered by a wideband filter and a plurality of narrowband filters. The wideband filters pass all predetermined groups of harmonics and corresponding sidebands and/or ringing frequencies of interest. In particular, the voltage and waveforms filtered by the wideband filter is then sampled by ADCs and all the remaining steps of this method are performed digitally.

In step 1030, voltage and current waveforms filtered by the wideband filter are multiplied by each other sample by sample to calculate the wideband power over the entire frequency spectrum of interest. Further, the RMS voltage and RMS current are also determined over the entire frequency spectrum of interest. The wideband power, the RMS voltage, and the RMS current are then passed through a low pass filter to filter out noise. The average RMS voltage and current are referred to as the RMS voltage $V_{RMS}$ and the RMS current $I_{RMS}$.

In step 1040, the plurality of narrowband filters are applied to the voltage and current waveforms filtered by the wideband filter to obtain phase and magnitude information at the group of frequencies, i.e., the fundamental, harmonic, or ringing frequencies. The magnitude information is an RMS voltage $V_{mag\_i}$ and an RMS current $I_{mag\_i}$ at each frequency $f_i$ among the frequencies of interest and the phase information is a voltage phase $\phi_{V\_i}$ and a current phase $\phi_{I\_i}$ at each frequency $f_i$ among the frequencies of interest.

In step 1050, cable compensation is performed by using the two-port network system described above. As described above with respect FIG. 7B, the RMS voltage $V_{mag\_i}$ and the RMS current $I_{mag\_i}$ are converted to rectangular form by using equations (3) and (4) to obtain the RMS voltage and current at the tissue. The cable compensation may be performed at a single frequency. The single frequency may be selected by comparing the magnitude of the RMS voltage or current. In other words, the selected frequency may have the greatest RMS voltage magnitude or the greatest RMS current magnitude.

In step 1060, power consumed by the tissue being treated is calculated. This is performed by subtracting the power loss from the average power. The power loss is calculated as follows:

$$P_{Loss}=I_{RMS}^2 \cdot Re(Z_{Src}), \tag{18}$$

where $P_{Loss}$ is the power loss in the generator, $I_{RMS}$ is the RMS current passing through the impedance of the generator, and $Re(Z_{Src})$ is the real part of the source impedance or simply the resistance value of source resistor $R_{Src}$. The power consumed in the tissue is then calculated as follows:

$$P_{Tissue}=P_{Avg}-P_{Loss}, \tag{19}$$

where $P_{Tissue}$ is the power consumed in the tissue and $P_{ave}$ is the average power.

In step 1070, the impedance of the tissue may be calculated at a single frequency according to the cable compensation process described above. The single frequency is selected as a frequency having the highest magnitude. The single frequency may be the fundamental frequency, a harmonic frequency, or a ringing frequency. The tissue impedance is calculated by using equation (13). When the tissue impedance is calculated, the RMS voltage across the tissue and the RMS current passing through the tissue are calculated according to the following equations:

$$V_{RMS\_Tissue} = \sqrt{P_{Tissue} \cdot |Z_{Tissue}|}, \tag{20}$$

$$I_{RMS\_Tissue} = \sqrt{\frac{P_{Tissue}}{|Z_{Tissue}|}}, \tag{21}$$

where $V_{RMS\_Tissue}$ is the RMS voltage across the tissue, $|Z_{Tissue}|$ is the magnitude of the tissue impedance, and $I_{RMS\_Tissue}$ is the RMS current passing through the tissue.

In embodiments, when the tissue load is near zero or infinity, the medium-band power may go to zero, which means that the $V_{RMS\_tissue}$ or $I_{RMS\_tissue}$ measurement is no longer correct. This may be addressed by a switch such that, when the narrowband impedance is less than a low threshold or greater than a high threshold, the $V_{RMS\_tissue}$ and $I_{RMS\_tissue}$ are replaced by the uncompensated RMS voltage and current, $V_{RMS}$ and $I_{RMS}$, which are measured at the sensor.

Although the illustrative embodiments of the present disclosure have been described herein with reference to the accompanying drawings, it is to be understood that the disclosure is not limited to those precise embodiments, and that various other changes and modification may be effected therein by one skilled in the art without departing from the scope or spirit of the disclosure.

What is claimed is:

1. An electrosurgical generator comprising:
   an output stage configured to generate energy;
   an electrosurgical cable configured to transmit the generated energy to tissue for treating tissue;
   a voltage sensor configured to sense a voltage waveform of the generated energy at the output stage;
   a current sensor configured to sense a current waveform of the generated energy at the output stage;
   a first medium-band filter configured to pass the sensed voltage waveform having at least one frequency within a first medium-band range of frequencies including a harmonic frequency;
   a second medium-band filter configured to pass the sensed current waveform having at least one frequency within the first medium-band range of frequencies including the harmonic frequency;
   a first narrowband filter configured to obtain narrowband phase and magnitude values of at least one frequency of the sensed voltage waveform within the first medium-band range of frequencies; and
   a second narrowband filter configured to obtain narrowband phase and magnitude values of at least one frequency of the sensed current waveform within the first medium-band range of frequencies; and
   a signal processor configured to:
      determine medium-band root-mean-square (RMS) voltage and current values based on the sensed voltage and current waveforms filtered by the first and second medium-band filters;
      estimate impedance of the tissue based on the narrowband magnitude and phase and the medium-band RMS voltage and current values; and
      generate a control signal to control the output stage to generate energy based on the estimated impedance of the tissue.

2. The electrosurgical generator according to claim 1, wherein the voltage and current waveforms include harmonic distortion caused by capacitance of the electrosurgical cable.

3. The electrosurgical generator according to claim 2, further comprising:
   a third medium-band filter configured to pass the sensed voltage waveform having a frequency within a second medium-band range of frequencies including a third harmonic frequency;
   a fourth medium-band filter configured to pass the sensed current waveform within the second medium-band range of frequencies including the third harmonic frequency;
   a third narrowband filter configured to obtain narrowband phase and magnitude values of at least one frequency of the sensed voltage waveform within the second medium-band range of frequencies; and
   a fourth narrowband filter configured to obtain narrowband phase and magnitude values of at least one frequency of the sensed current waveform within the second medium-band range of frequencies,
   wherein the harmonic frequency is a fundamental frequency.

4. The electrosurgical generator according to claim 3, further comprising:
   a fifth medium-band filter configured to pass the sensed voltage waveform within a third medium-band range of frequencies including a fifth harmonic frequency;
   a sixth medium-band filter configured to pass the sensed current waveform within the third medium-band range of frequencies including the fifth harmonic frequency;
   a fifth narrowband filter configured to obtain narrowband phase and magnitude values of at least one frequency of the sensed voltage waveform within the third medium-band range of frequencies; and
   a sixth narrowband filter configured to obtain narrowband phase and magnitude values of at least one frequency of the sensed current waveform within the third medium-band range of frequencies.

5. The electrosurgical generator according to claim 3, wherein the signal processor further determines medium-band RMS voltage and current values based on the sensed voltage and current waveforms filtered by the third and fourth medium-band filters, calculates a total RMS voltage value by summing the RMS voltage values, and calculates a total RMS current value by summing the RMS current values.

6. The electrosurgical generator according to claim 5, wherein the signal processor selects frequencies from within the first and second medium-band ranges of frequencies and calculates weights for the medium-band RMS voltage and current values at the selected frequencies based on the narrowband magnitudes.

7. The electrosurgical generator according to claim 6, wherein the weights are percentages based on ratios between the medium-band RMS voltage values of a medium-band range of frequencies including a selected frequency and the total RMS voltage value, or the ratios between the medium-band RMS current values of a medium-band range of frequencies including a selected frequency and the total RMS current value.

8. The electrosurgical generator according to claim 6, wherein the signal processor calculates weighted RMS voltage and current values at the selected frequencies and calculates weighted powers based on the weighted RMS voltage and current values.

9. The electrosurgical generator according to claim 8, wherein the RMS voltage values and the RMS current values are calculated by using a two-port network model of the electrosurgical cable, and
   wherein power consumed by the tissue is calculated by adding the weighted powers.

10. The electrosurgical generator according to claim 6, wherein the signal processor calculates the impedance of the tissue at a selected frequency that has a highest weighted magnitude.

11. A method for electrosurgical cable compensation, the method comprising:
    generating, by an output stage, energy;
    transmitting, via an electrosurgical cable, the energy to tissue for treating the tissue;
    sensing voltage and current waveforms of the energy generated by the output stage;
    passing the sensed voltage and current waveforms within a first medium-band range of frequencies including a harmonic frequency;

obtaining narrowband phase and magnitude values of at least one frequency of the sensed voltage and current waveforms within the first medium-band range of frequencies;

determining medium-band root-mean-square (RMS) voltage and current values based on the passed voltage and current waveforms within the first medium-band range of frequencies;

estimating an impedance of the tissue based on the narrowband magnitude and phase and the medium-band RMS voltage and current values; and generating a control signal to control the output stage to generate energy based on the estimated impedance of the tissue.

12. The method according to claim 11, further comprising:

passing the sensed voltage and current waveforms having frequencies within a second medium-band range of frequencies including a third harmonic frequency; and obtaining narrowband phase and magnitude values of at least one frequency of the sensed voltage and current waveforms within the second medium-band range of frequencies.

13. The method according to claim 12, further comprising:

passing the sensed voltage and current waveforms within a third medium-band range of frequencies including a fifth harmonic frequency; and obtaining narrowband phase and magnitude values of at least one frequency of the sensed voltage and current waveforms within the third medium-band range of frequencies.

14. The method according to claim 12, further comprising:

determining medium-band root-mean-square (RMS) voltage and current values based on the passed voltage and current waveforms within the second medium-band range of frequencies;

calculating a total RMS voltage value by summing medium-band RMS voltage values;

calculating a total RMS current value by summing medium-band RMS current values;

selecting frequencies from within the first and second medium-band ranges of frequencies; and calculating weights for the medium-band RMS voltage and current values at the selected frequencies based on the narrowband magnitude values.

15. The method according to claim 14, wherein the weights are percentages based on ratios between the medium-band RMS voltage values of a medium-band range of frequencies including a selected frequency and the total RMS voltage value, or ratios between the medium-band RMS current values of a medium-band range of frequencies including a selected a frequency and the total RMS current value.

16. The method according to claim 14, further comprising:

calculating weighted RMS voltage and current values for the selected frequencies; and calculating weighted powers based on the weighted RMS voltage and current values to obtain power consumed in the tissue.

17. The method according to claim 16, wherein the power consumed in the tissue is calculated by adding the weighted powers for the selected frequencies.

18. The method according to claim 14, further comprising calculating the impedance of the tissue at a selected frequency that has a highest weighted magnitude.

19. The method according to claim 11, further comprising:

calculating an average power based on the medium-band RMS voltage and current values to obtain an average power for the first medium-band range of frequencies; and calculating a power loss in the electrosurgical cable based on a known impedance of the electrosurgical cable and the medium-band RMS voltage or current value by subtracting the power loss from the average power.

20. The method according to claim 19, further comprising:

calculating narrowband impedance of the tissue at a frequency that has a highest narrowband magnitude;

calculating a power consumed in the tissue by subtracting the power loss from the average power; and compensating the impedance of the tissue based on the power consumed in the tissue.

* * * * *